United States Patent
Kitagawa et al.

(10) Patent No.: US 7,931,863 B2
(45) Date of Patent: Apr. 26, 2011

(54) SAMPLE ANALYZER

(75) Inventors: Nobuhiro Kitagawa, Akashi (JP); Shuhei Kaneko, Kobe (JP); Kyozo Fujita, Hamburg (DE)

(73) Assignee: Sysmex Corporation, Kobe-shi (JP)

( * ) Notice: Subject to any disclaimer, the term of this patent is extended or adjusted under 35 U.S.C. 154(b) by 582 days.

(21) Appl. No.: 11/824,228

(22) Filed: Jun. 29, 2007

(65) Prior Publication Data
US 2008/0014118 A1    Jan. 17, 2008

(30) Foreign Application Priority Data

Jun. 30, 2006  (JP) ................... 2006-180579
May 23, 2007  (JP) ................... 2007-137044

(51) Int. Cl.
  G01N 21/00  (2006.01)
  G01N 31/00  (2006.01)
  G01N 33/00  (2006.01)
  G01N 35/00  (2006.01)
(52) U.S. Cl. ............... 422/67; 422/63; 422/64; 436/43
(58) Field of Classification Search ........... 422/64
  See application file for complete search history.

(56) References Cited

U.S. PATENT DOCUMENTS

| | | | | |
|---|---|---|---|---|
| 4,166,095 A | * | 8/1979 | Kling et al. | 422/67 |
| 4,849,177 A | * | 7/1989 | Jordan | 422/64 |
| 5,316,726 A | * | 5/1994 | Babson et al. | 422/65 |
| 5,424,036 A | | 6/1995 | Ushikubo | |
| 5,827,479 A | | 10/1998 | Yamazaki et al. | |
| 2004/0057872 A1 | * | 3/2004 | Shibuya et al. | 422/64 |
| 2005/0013736 A1 | * | 1/2005 | McKeever | 422/63 |
| 2005/0207938 A1 | * | 9/2005 | Hanawa et al. | 422/64 |

FOREIGN PATENT DOCUMENTS

| | | |
|---|---|---|
| EP | 0845674 A1 | 6/1998 |
| EP | 1376138 A2 | 1/2004 |
| EP | 1560028 A2 | 8/2005 |
| JP | 2000-321283 | 11/2000 |

OTHER PUBLICATIONS

European Search Report for Application No. EP 07012708 dated Oct. 19, 2007.

* cited by examiner

*Primary Examiner* — Jyoti Nagpaul
*Assistant Examiner* — Charles Hammond
(74) *Attorney, Agent, or Firm* — Brinks Hofer Gilson & Lione

(57) ABSTRACT

The present invention is to present a sample analyzer which is able to move a reagent container containing a reagent which a user desires to replace to a pick up position. The sample analyzer comprises: a holding section comprising a plurality of holding regions for holding reagent containers, and being capable of moving the holding regions; analyzing means for analyzing a measurement sample prepared by mixing a sample and the reagent contained in the reagent container held by the holding section; receiving means for receiving a specification of a holding region from the plurality of holding regions to replace or add a reagent; and control means for controlling the holding section so as to move the specified holding region to a replacement-addition position at which the reagent is replaced or added, when the receiving means receives the specification of the holding region.

11 Claims, 22 Drawing Sheets

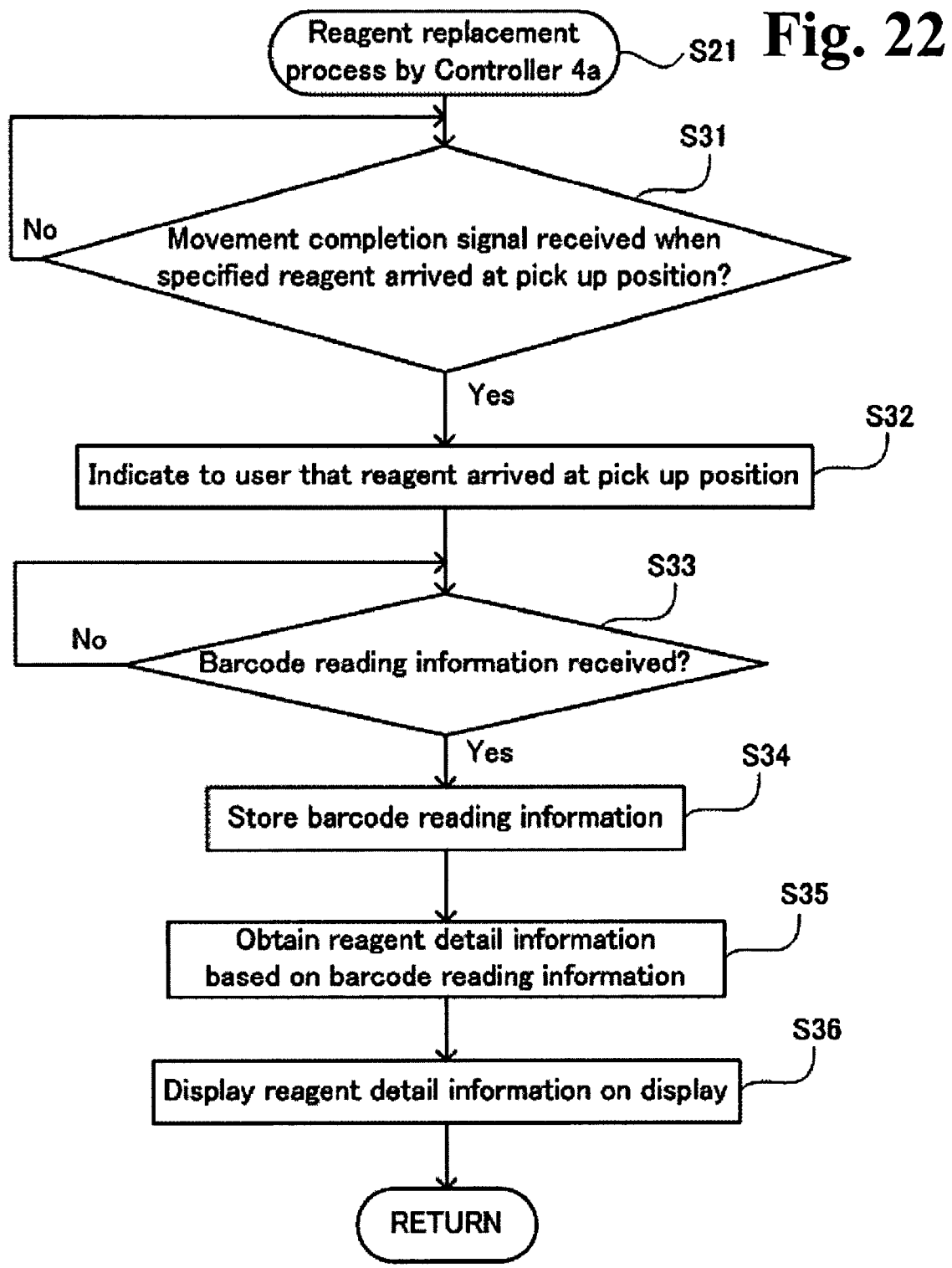

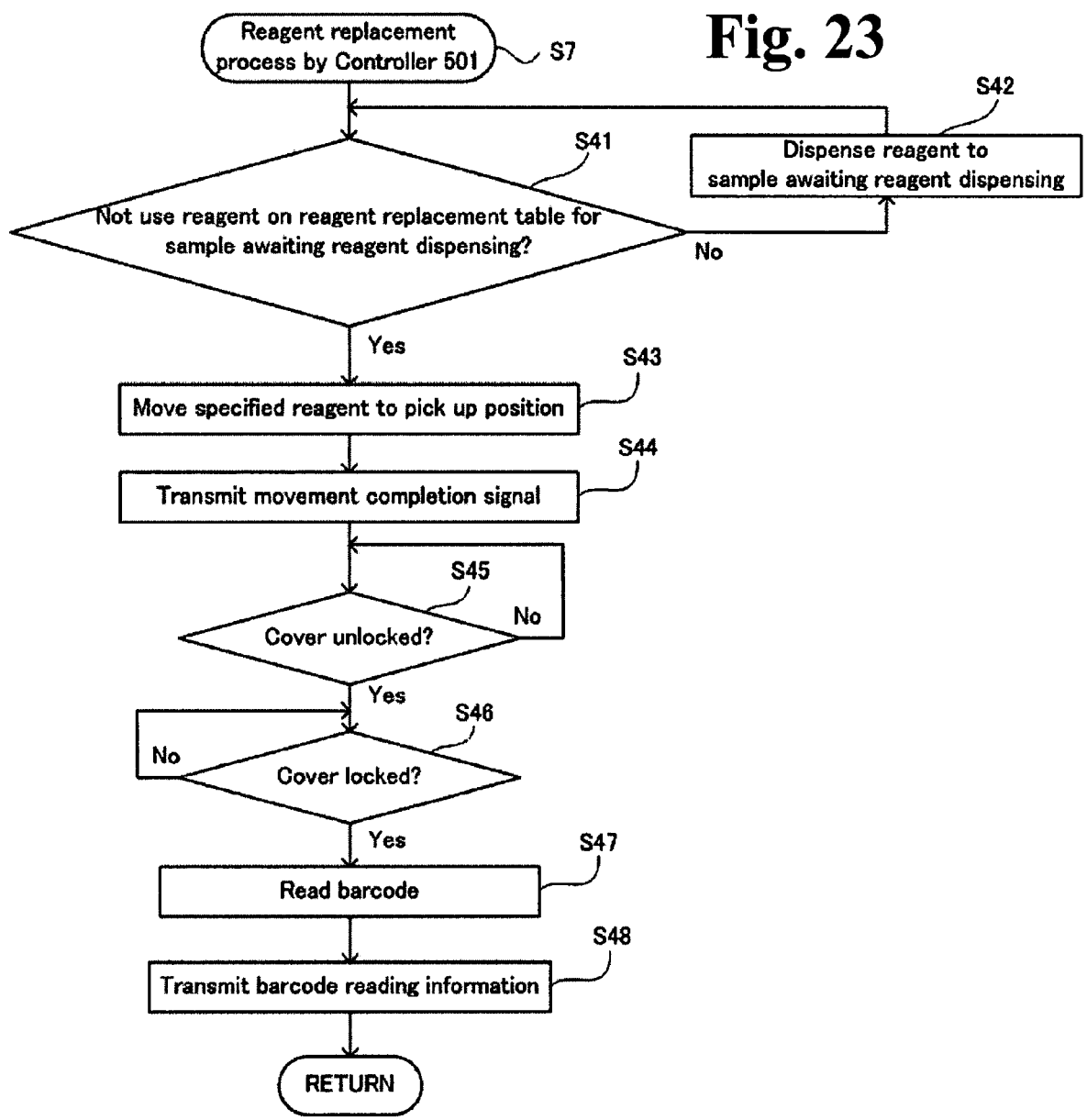

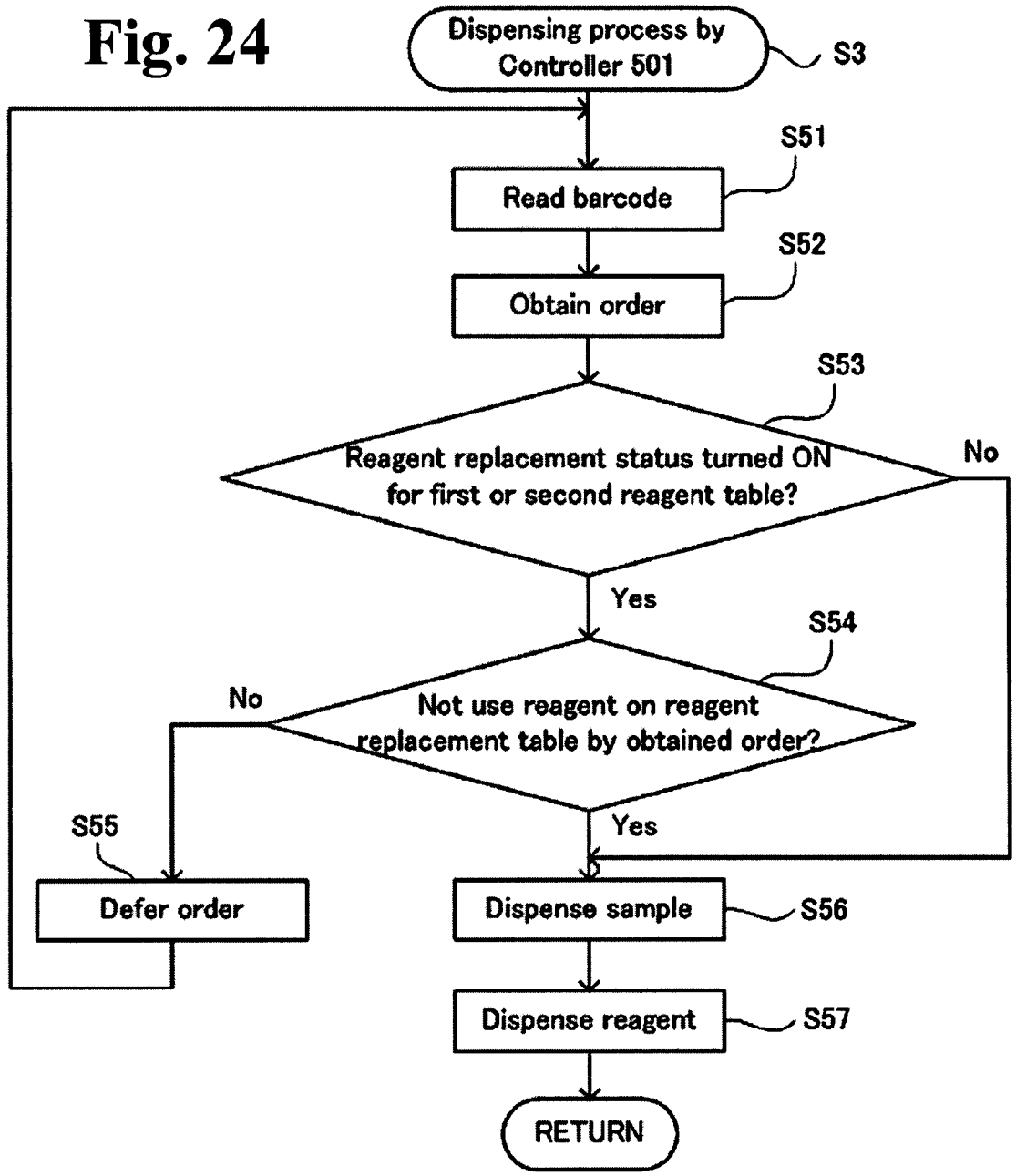

SAMPLE ANALYZER

RELATED APPLICATIONS

This application claims priority under 35 U.S.C. §119 to Japanese Patent Application Nos. JP2006-180579 filed Jun. 30, 2006, and JP2007-137044 filed May 23, 2007, the entire content of which is hereby incorporated by reference.

FIELD OF THE INVENTION

The present invention relates to a sample analyzer, and specifically relates to a sample analyzer provided with a holding section being capable of holding a reagent container which contains a reagent.

BACKGROUND

Japanese Laid-Open Patent Publication No. 2000-321283 discloses conventional sample analyzers which have a movable holding section being capable of holding reagent containers that contain reagent.

The sample analyzer disclosed in Japanese Laid-Open Patent Publication No. 2000-321283 is provided with a housing means for housing a plurality of reagent bottles that contain reagent, measuring means for measuring the amount of residual reagent remaining in reagent bottles which are housed in the housing means, specifying means for specifying reagent bottles to be replaced based on the measurement results of the measuring means, and moving means for moving a reagent bottle specified by the specifying means to a predetermined position.

In sample analyzers that use a plurality of reagents, even though the amount of residual reagent remaining in a reagent container is insufficient for measurement of a sample, it is not always necessary to replace the reagent since the sample analyzers are able to hold a reserve reagent container containing the same reagent as the insufficient reagent. That is, insufficient reagent is not necessarily a target to be replaced. On the other hand, it is sometimes necessary to replace a reagent for reasons other than the insufficiency of the reagent. For example, a reagent whose validity date has expired needs to be replaced. Accordingly, a problem arises in the sample analyzer disclosed in Japanese Laid-Open Patent Publication No. 2000-321283 that a reagent container which contains a reagent which a user desires to replace is not always be moved to a predetermined position (pick up position) at which the container is able to be picked up inasmuch as the container containing insufficient reagent is automatically moved to the pick up position when the sample analyzer detects that reagent within the reagent container is insufficient.

SUMMARY

The scope of the present invention is defined solely by the appended claims, and is not affected to any degree by the statements within this summary.

A first aspect of the present invention is a sample analyzer for analyzing a sample, comprising: a holding section comprising a plurality of holding regions for holding reagent containers, each of the reagent containers containing a reagent, and being capable of moving the holding regions; analyzing means for analyzing a measurement sample prepared by mixing a sample and the reagent contained in the reagent container held by the holding section; receiving means for receiving a specification of a holding region from the plurality of holding regions to replace or add a reagent; and control means for controlling the holding section so as to move the specified holding region to a replacement-addition position at which the reagent is replaced or added, when the receiving means receives the specification of the holding region.

A second aspect of the present invention is a sample analyzer for analyzing a sample, comprising: a movable holding section for holding a plurality of reagent containers, each of the reagent containers containing a reagent; analyzing means for analyzing a measurement sample prepared by mixing a sample and the reagent contained in the reagent container held by the holding section; receiving means for receiving a specification of a reagent from reagents contained in the plurality of reagent containers held by the holding section; and control means for controlling the holding section so as to move the reagent container containing the specified reagent to a pick up position at which the reagent container is picked up, when the receiving means receives the specification of the reagent.

A third aspect of the present invention is A sample analyzer for analyzing a sample, comprising: a movable holding section for holding a plurality of reagent racks for holding reagent containers, each of the reagent containers containing a reagent; analyzing means for analyzing a measurement sample prepared by mixing a sample and the reagent contained in the reagent container held in the reagent rack; receiving means for receiving a specification of a reagent rack from the plurality of reagent racks held by the holding section; and control means for controlling the holding section so as to move the specified reagent rack to a pick up position at which the reagent rack is picked up, when the receiving means receives the specification of the reagent rack.

BRIEF DESCRIPTION OF THE DRAWINGS

FIG. 22 is a flow chart illustrating the reagent replacement process performed by the controller of the embodiment of the sample analyzer of the present invention;

FIG. 23 is a flow chart illustrating the reagent replacement process performed by the controller of the measuring unit of the embodiment of the sample analyzer of the present invention; and FIG. 24 is a flow chart illustrating the dispensing process performed by the controller of the measuring unit of the embodiment of the sample analyzer of the present invention.

DETAILED DESCRIPTION OF THE PREFERRED EMBODIMENT

The embodiments of the present invention are described hereinafter based on the drawings.

The structure of the sample analyzer 1 as an embodiment of the present invention is described below with reference to FIGS. 1 through 20.

The embodiment of the sample analyzer 1 of the present invention optically measures and analyzes the amount and activity of specific substances found in blood related to coagulation and fibrinolysis, and uses blood plasma as a sample. In the sample analyzer 1 of the present embodiment, such optical measurement (main measurement) of specimens are performed using the coagulation time method, synthetic substrate method, and immunoturbidity method. The coagulation time method used in the present embodiment detects and measures the change in the transmission light during the sample coagulation process. Measurement items include PT (prothrombin time), APTT (active partial thromboplastin time), and Fbg (fibrinogen content) and the like. Measurement items of the synthetic substrate method include ATIII and the like, and those of the immunoturbidity method include D-dimer, FDP and the like.

Figure 1:
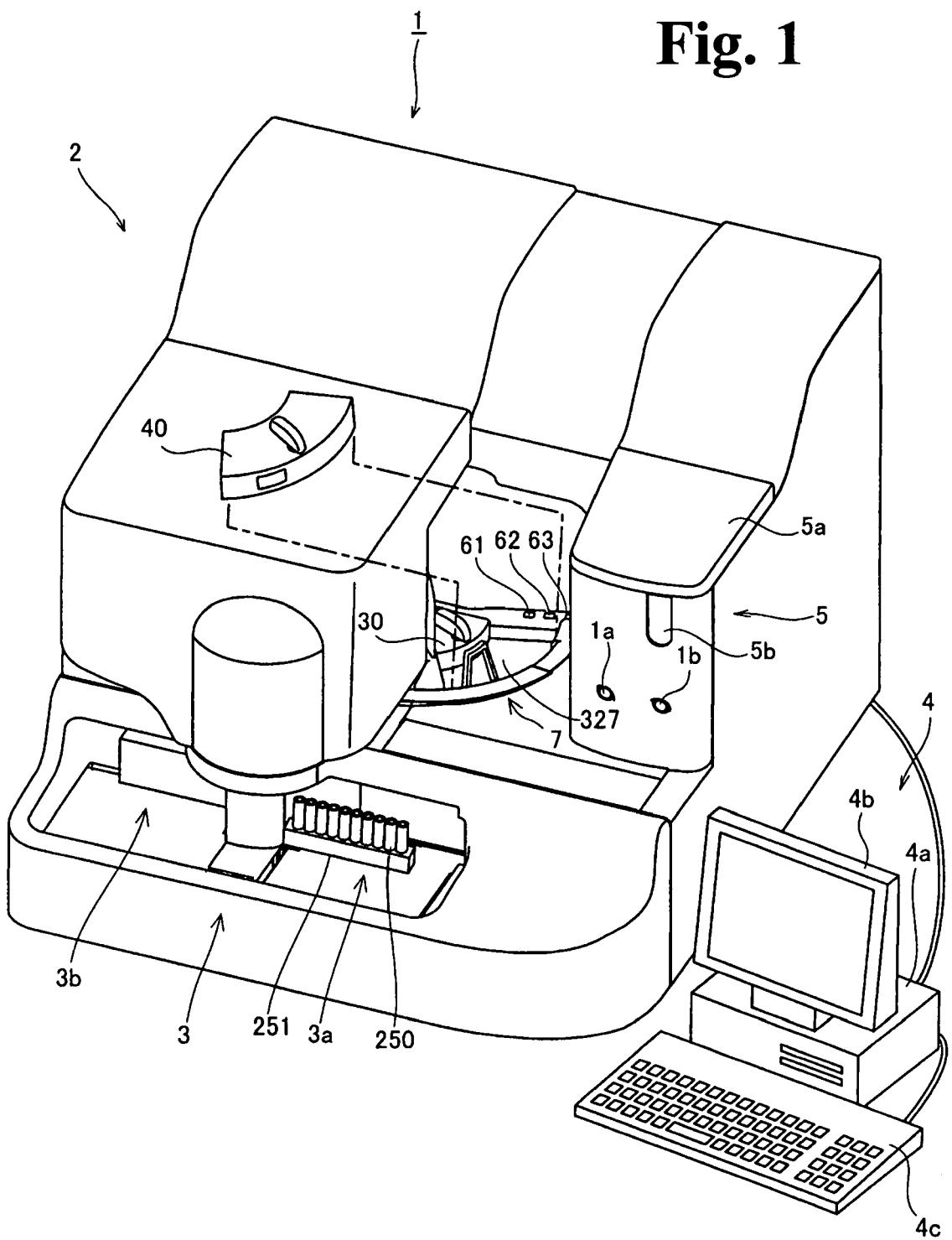
FIG. 1 is a perspective view showing the general structure of an embodiment of the sample analyzer of the present invention.
Figure 2:
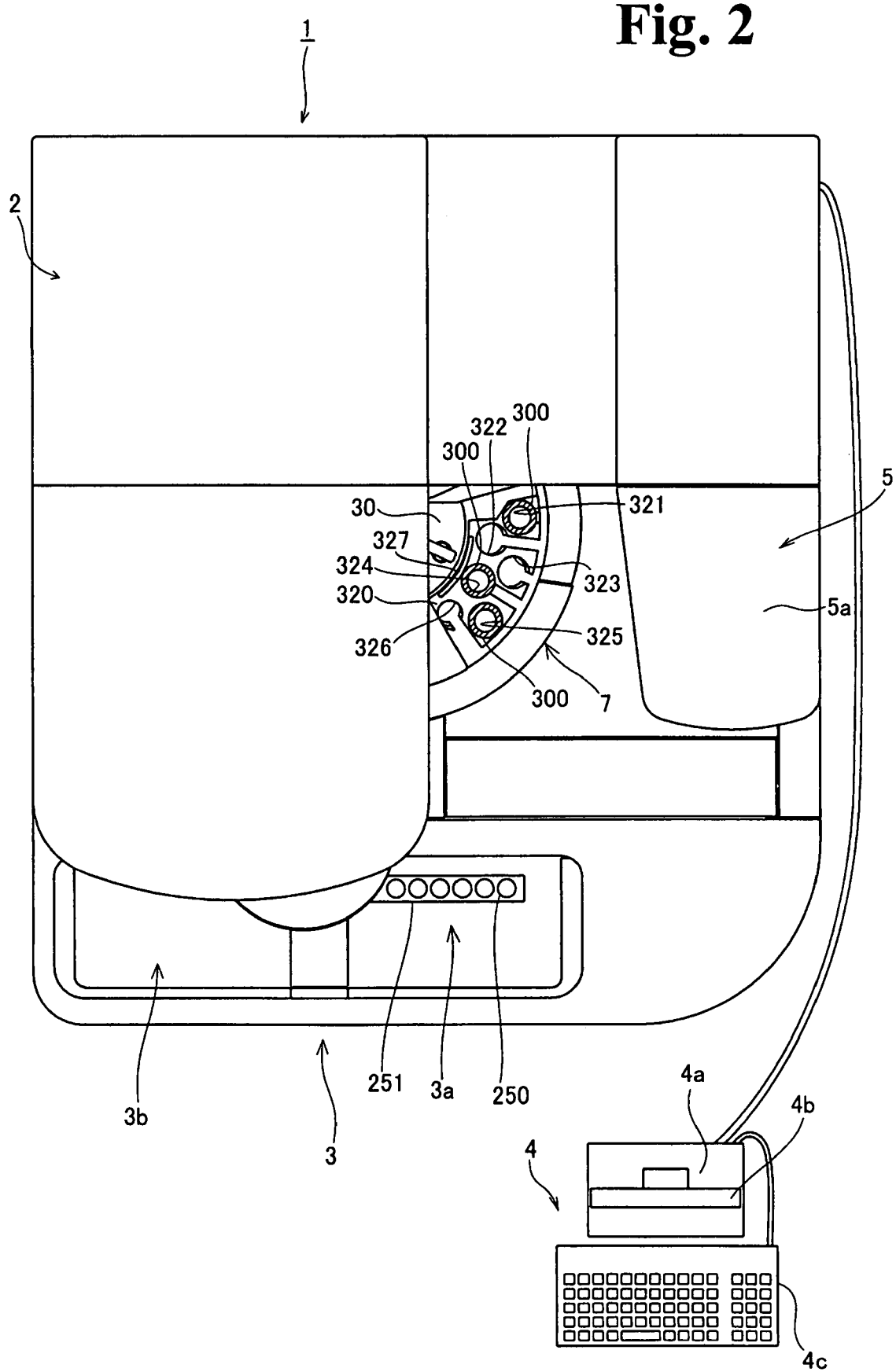
FIG. 2 is a top view of the sample analyzer of FIG. 1.

As shown in FIGS. 1 and 2, the sample analyzer 1 is configured by a measuring unit 2, sample transporting unit 3 disposed on the front side of the measuring unit 2, and a control unit 4 which is electrically connected to the measuring unit 2. The measuring unit 2 is provided with a cuvette acceptor 5 for inserting a cuvette 200 (refer to FIG. 4), which is a sample container, when performing a measurement. The cuvette acceptor 5 is provided with a cover 5a that is able to be opened and closed, and a window 5b through which the interior of the cuvette insertion part 5 is able to be viewed.

Furthermore, an emergency stop button 1a, and measurement start button 1b are provided on the front side of the cuvette acceptor 5. The cover 5a (refer to FIG. 1) is provided so a cuvette 200 is able to be inserted into the first hopper 171a (refer to FIG. 4) of a cuvette supplier 170, which is described later. A user is able to visually monitor the remaining quantity of cuvettes 200 stored in the first hopper 171a (refer to FIG. 4) through the window 5b. The emergency stop button 1a (refer to FIG. 1) functions to stop a measurement during an emergency. The measurement start button 1b (refer to FIG. 1) is configured so as to start a measurement when the button is pressed. Thus, a user is able to start a measurement immediately after a cuvette 200 has been inserted. Starting and stopping of a measurement may also be accomplished by an operation performed by the control unit 4.

The control unit 4 is configured by a personal computer 401 (PC), and includes a controller 4a, display 4b, and keyboard 4c, as shown in FIGS. 1 and 2. The controller 4a functions to control the operations of the measuring unit 2 and transporting unit 3, and analyzes the optical information of samples obtained by the measuring unit 2. The controller 4a is configured by a CPU, ROM, RAM and the like. Furthermore, the display 4b is provided to display information relating to interference substances (hemoglobin, bilirubin, chyle (fats)) present in a sample, and analysis results obtained by the controller 4a.

Figure 6:
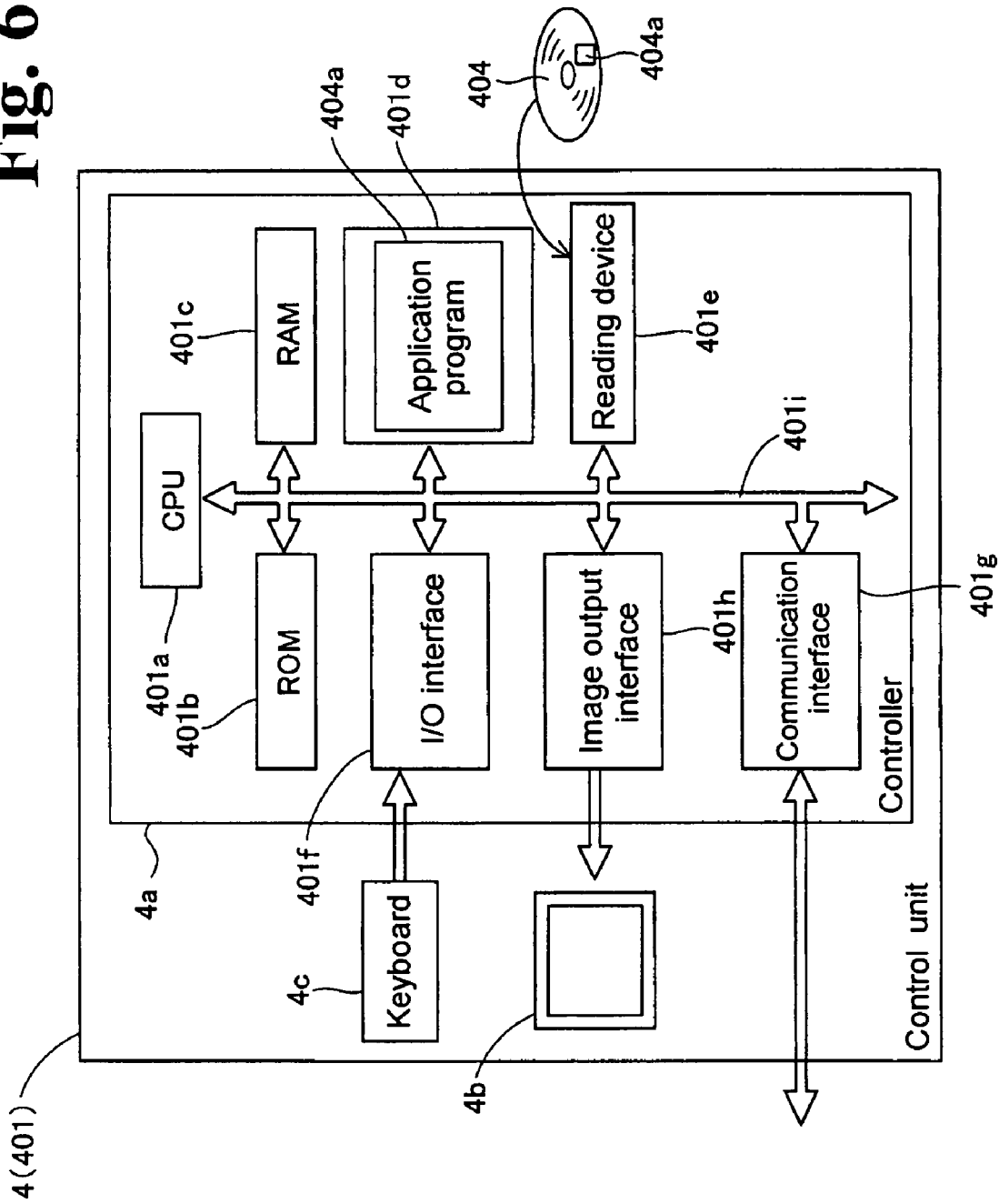
FIG. 6 is a block diagram showing the control unit of the embodiment of the sample analyzer of the present invention.

The structure of the control unit 4 is described below. As shown in FIG. 6, the controller 4a is mainly configured by a CPU 401a, ROM 401b, RAM 401c, hard disk 401d, reading device 401e, I/O interface 401f, communication interface 401g, and image output interface 401h. The CPU 401a, ROM 401b, RAM 401c, hard disk 401d, reading device 401e, I/O interface 401f, communication interface 401g, and image output interface 401h are connected by a bus 401i.

The CPU 401a is capable of executing computer programs stored in the ROM 401b, and computer programs loaded in the RAM 401c. The computer 401 functions as the control unit 4 when the CPU 401a executes an application program 404a described later.

The ROM 401b is configured by a mask ROM, PROM, EPROM, EEPROM or the like, and stores computer programs executed by the CPU 401a and data and the like used in conjunction therewith.

The RAM 401c is configured by SRAM, DRAM or the like. The RAM 401c is used when reading the computer program recorded in the ROM 401b and on the hard disc 401d. The RAM 401c is further used as a work area of the CPU 401a when these computer programs are being executed.

The hard disc 401d contains various installed computer programs to be executed by the CPU 401a such as an operating system and application programs and the like, and data used in the execution of these computer programs. Also installed on the hard disk 401d is the application program 404a used to calculate the presence and concentration of interference substances in the present embodiment.

The reading device 401e is configured by a floppy disk drive, CD-ROM drive, DVD-ROM drive or the like, and is capable of reading the computer programs and data stored on a portable recording medium 404. Furthermore, the portable recording medium 404 may also store the application program 404a in the present embodiment; the computer 401 is capable of reading the application program 404a from the portable recording medium 404 and installing the application program 404a on the hard disk 401d.

Not only may the application program 404a be provided by the portable recording medium 404, it also may be provided from an external device connected to the computer 401 so as to be capable of communication over an electric communication line by means of the electric communication line (wire line or wireless). For example, the application program 404a may be stored on the hard disk of a server computer connected to the internet, such that the computer 401a is able to access the server computer and download the application program 404a, and then install the application program 404a on the hard disk 401d.

Also installed on the hard disk 401d is an operating system providing a graphical user interface, such as, for example, Windows (registered trademark) of Microsoft Corporation, U.S.A. In the following description, the application program 404a of the present embodiment operates on such an operating system.

The I/O interface 401f is configured by a serial interface such as a USB, IEEE1394, RS232C or the like, parallel interface such as SCSI, IDE, IEEE1284 or the like, analog interface such as a D/A converter, A/D converter or the like. The keyboard 4c is connected to the I/O interface 401f, such that a user is able to input data in the computer 401 using the keyboard 4c.

The communication interface 401g is, for example, and Ethernet (registered trademark) interface. The computer 401 is able to transmit and receive data to and from the measuring unit 2 using a predetermined communication protocol via the communication interface 401g.

The image output interface 401h is connected to the display 4b configured by an LCD, CRT or the like, such that image signals corresponding to the image data received from the CPU 401a is able to be output to the display 4b. The display 4b displays an image (screen) in accordance with the input image signals.

Figure 7:
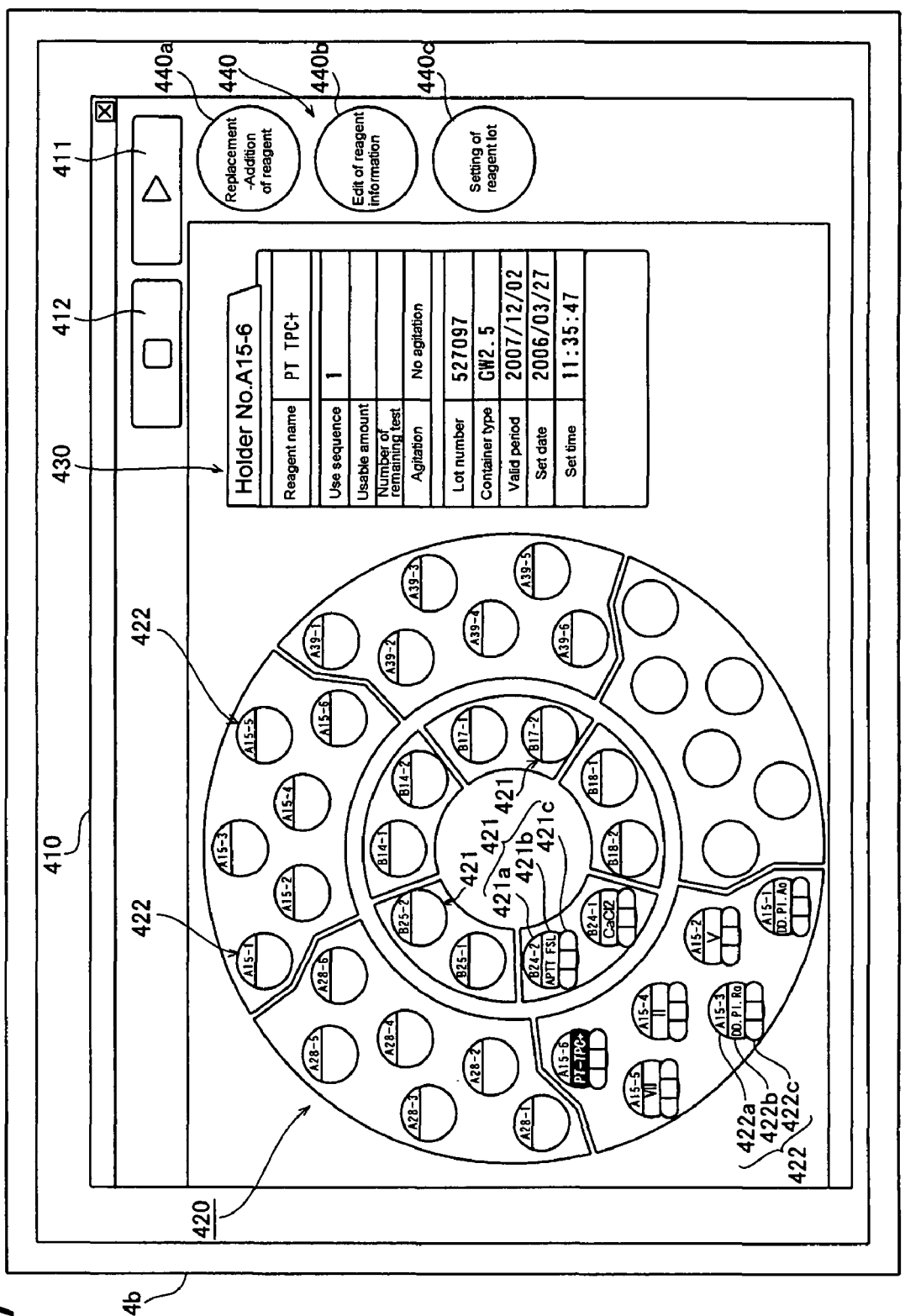
FIG. 7 shows the reagent placing screen displayed on the display of the control unit of the embodiment of the present invention.

In the present embodiment, as shown in FIG. 7, the display 4b is capable of displaying a reagent placement screen 410 that displays the layout of reagents in the reagent preserving section 6, which is described later. The reagent placement screen 410 has a reagent placement display region 420, reagent information display region 430, and command display region 440. The reagent placement screen 410 is provided with a measurement start button 411 for starting the measurement process in the sample analyzer 1, and a measurement stop button 412 for stopping the measurement. The display 4b functions as a touch panel to allow selections and operations when a user directly touches a button or the like displayed on the reagent placing screen 410.

The reagent placement display region 420 includes a plurality of first reagent display regions 421 for displaying the reagents disposed on a first reagent table 11 which is described later, and a plurality of second reagent display regions 422 for displaying the reagents disposed on a second reagent table 12 which also described later. The first reagent display region 421 includes a position display 421a for displaying the position of the reagent, reagent name display 421b for displaying the name of the reagent, and remainder display 421c for displaying the residual amount of the reagent. The second reagent display region 422 includes a position display 422a for displaying the position of the reagent, reagent name display 422b for displaying the name of the reagent, and remainder display 422c for displaying the residual amount of the reagent. The positions of the reagent displayed in the reagent name displays 421a and 422a are displayed when the barcode reader 350 reads the barcodes 311b and 312b of the first reagent container rack 310, and the barcodes 321b through 326b of the second reagent container rack 320, which are described later. The reagent names displayed in the reagent name displays 421b and 422b are displayed by referencing a special table based on the values of the barcodes 300a of the reagent container 300 read by the barcode reader 350. Moreover, the residual amount of the reagent displayed in the remainder displays 421c and 422c are displayed based on values calculated from the number of aspirations of the reagent and type of container that contains the reagent.

Figure 5:
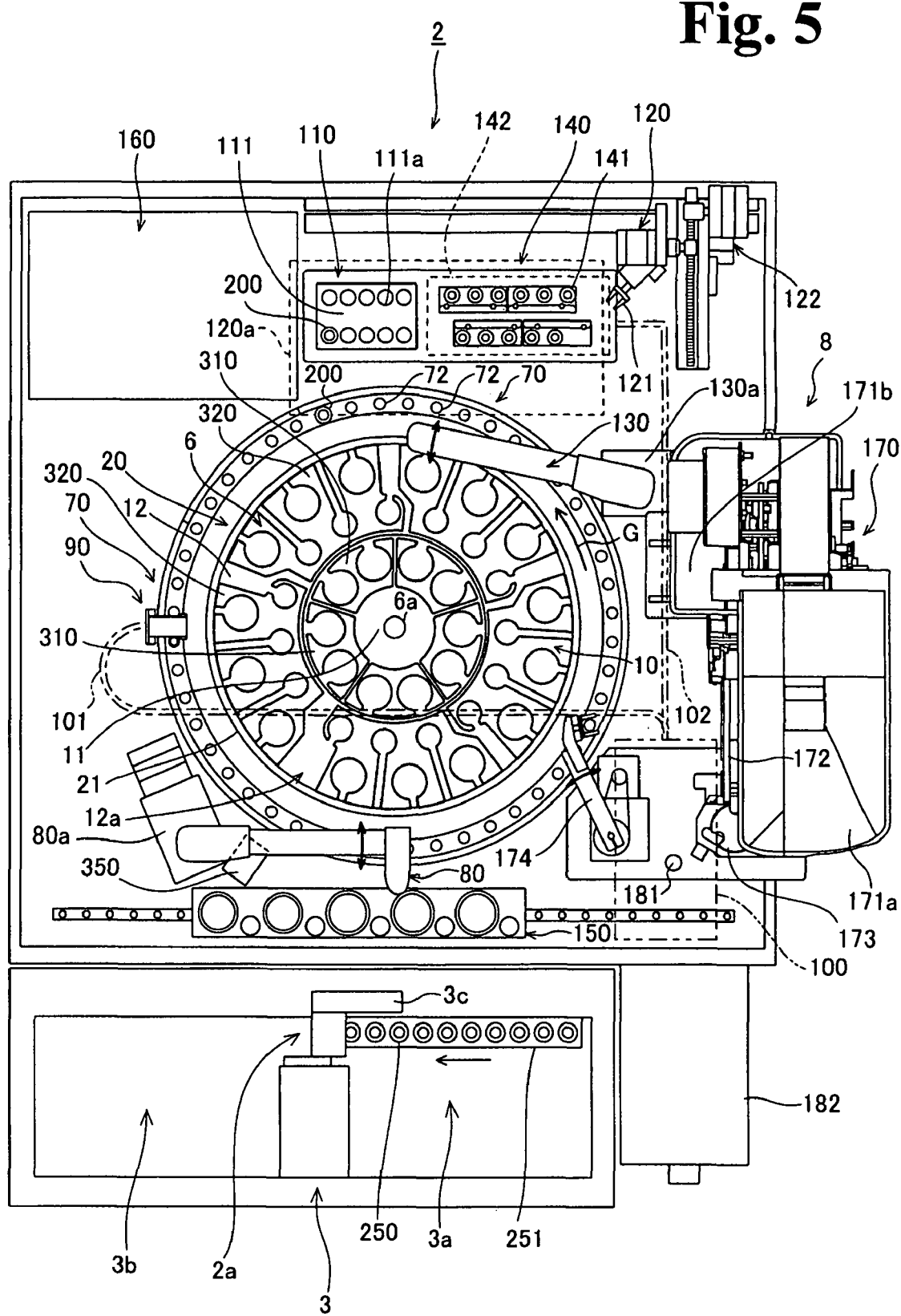
FIG. 5 is a top view showing the interior of the measuring unit and reagent preserving section shown in FIG. 4.

The first reagent display region 421 is divided in two parts in each of the regions corresponding to the five first reagent container racks 310 (refer to FIG. 5) which are each capable of holding two reagent containers 300 disposed on the first reagent table 11 (refer to FIG. 5). The second reagent display region 422 s divided in six parts in each of the regions corresponding to the five second reagent container racks 320 (refer to FIG. 5) which are each capable of holding six reagent containers 300 disposed on the second reagent table 12 (refer to FIG. 5). That is, it is possible to confirm on the reagent placement screen 410 how the reagents are placed, meaning at which positions on which reagent container rack (first reagent container rack 310 or second reagent container rack 320) and on which reagent table (first reagent table 11 or second reagent table 12).

When the first reagent container rack 310 or second reagent container rack 320 is not disposed on the first reagent table 11 or second reagent table 12, nothing is displayed in the first reagent display region 421 or second reagent display region 422. When the first reagent container rack 310 or second reagent container rack 320 is disposed on the first reagent table 11 or second reagent table 12, but the container rack does not hold a reagent container 300, only the position display 421a or position display 422a is displayed in the first reagent display region 421 or second reagent display region 422. This aspect is described more fully later.

The attribute information (holder number, reagent name, use sequence, usable residual amount (usable amount), number of remaining tests, agitation requirement, lot number, type of reagent container, reagent expiration date, installation date and time and the like) of the specified reagent is displayed in the first reagent display region 421 or second reagent display region 422. A user is able to determine the replacement period of the reagent by the reagent attribute information.

The command display region 440 includes a replace-add command button 440a for issuing instruction for the replacement or addition of reagent, edit button 440b for editing the reagent information, and reagent lot setting button 440c for manually entering the reagent lot. In the present embodiment, a first reagent container rack 310 or second reagent container rack 320 holding a reagent container 300 that contains a specified reagent is moved to a position at which it is able to be picked up from the sample analyzer 1 by selecting the replace-add command button 440a when a reagent has been specified. When adding reagent, the first reagent display region 421 or second reagent display region 422, in which a reagent is not disposed, is specified, and the replace-add button 440a is selected. Thus, the first reagent container rack 310 or second reagent container rack 320 that does not accommodate reagent is moved to the pick up position.

Figure 3:
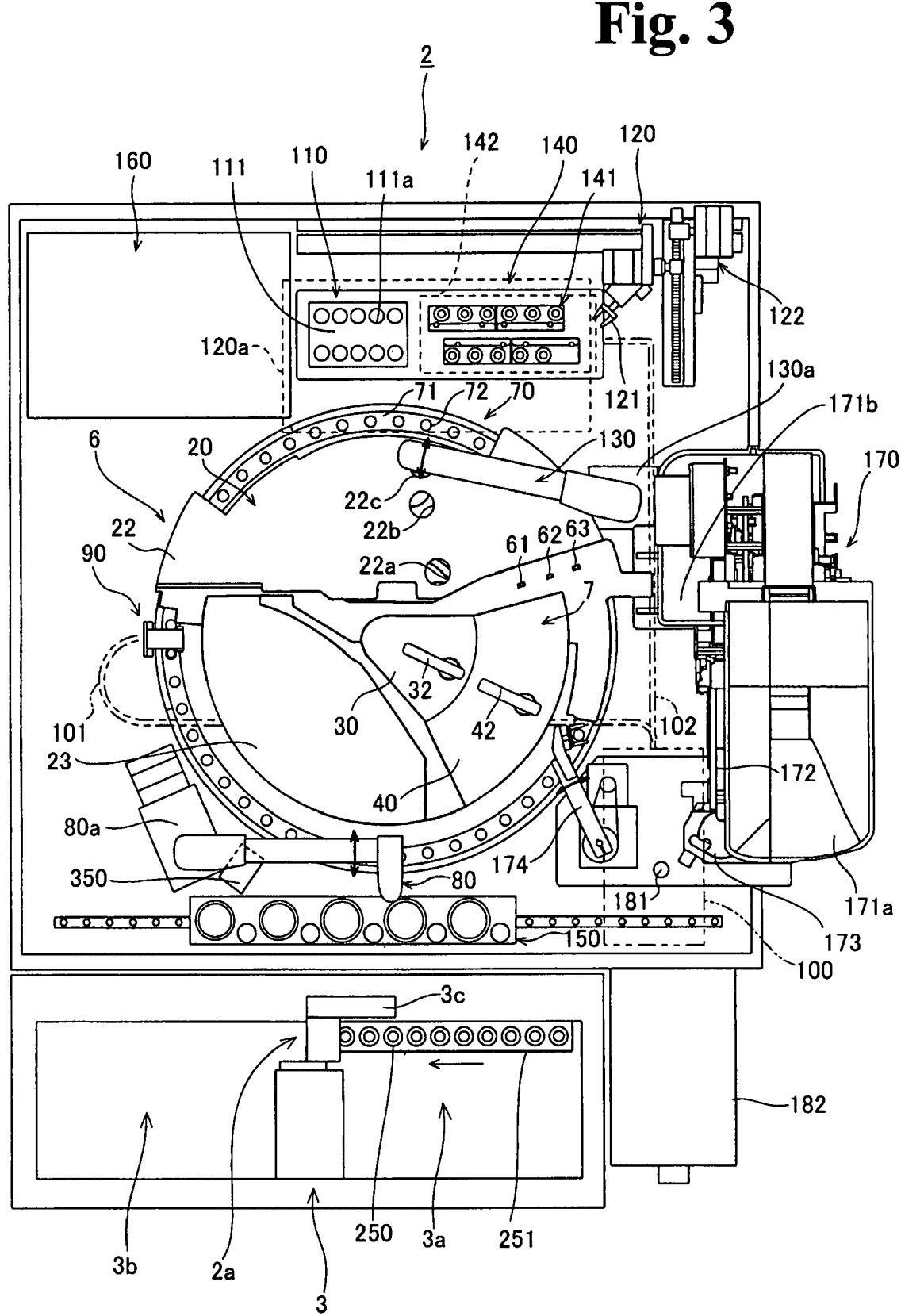
FIG. 3 is a top view of the measuring unit of the embodiment of the sample analyzer of the present invention.

As shown in FIGS. 1 through 3, the sample transporting unit 3 functions to transport the rack 251 that holds a plurality (ten in the present embodiment) of test tubes that contain samples to the aspirating position 2a (refer to FIG. 3) of the measuring unit 2 to supply sample to the measuring unit 2. Furthermore, the transport device 3 has a rack set region 3a that accommodates the racks 251 that hold the test tubes 250 containing unprocessed specimens, and a rack receiving region 3b that accommodates the racks 251 that hold test tubes 250 containing processed specimens.

The measuring unit 2 is capable of obtaining optical information related to a supplied sample by optically measuring the sample supplied from the transporting unit 3. In the present embodiment, a sample is dispensed from the test tube 250 disposed in the rack 251 of the transporting unit 3 into a cuvette 200 of the measuring unit 2, and is then optically measured as shown in FIG. 3, the measuring unit 2 includes a reagent storing part 6 and for storing reagent, and a reagent replacing part 7 for replacing or adding reagent.

Figure 19:
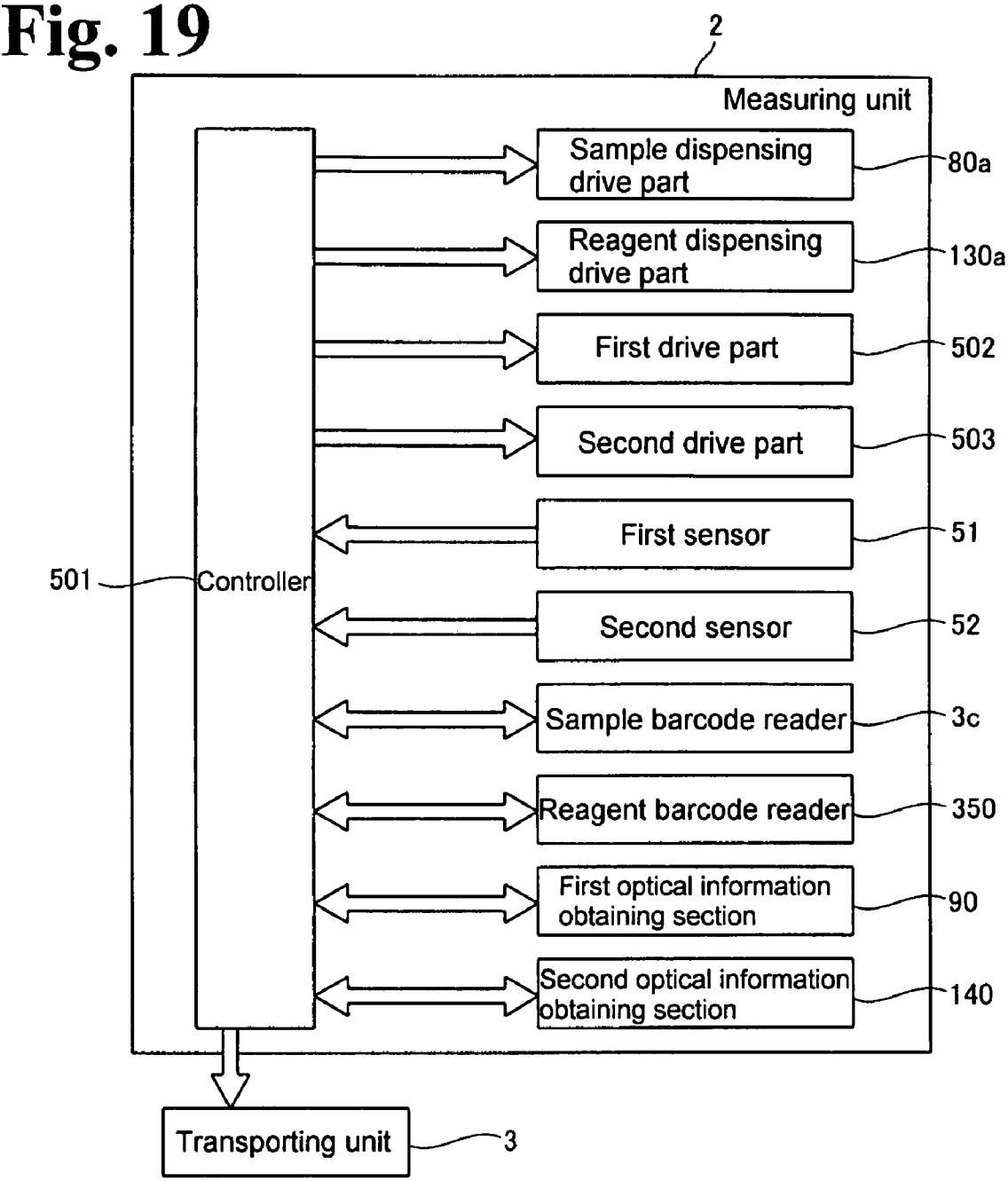
FIG. 19 is a block diagram of the embodiment of the sample analyzer of the present invention.

As shown in FIG. 19, the measuring unit 2 has a sample dispensing drive part 80a, sample dispensing drive part 130a, first drive part 502, second drive part 503, first sensor 51, second sensor 52, reagent barcode reader 350, sample barcode reader 3c, first optical information obtaining part 90, second optical information obtaining part 140, and a controller 501 that is electrically connected to transporting unit 3, etc.

The sample dispensing drive part 80a is provided with a stepping motor 80b that functions to raise, lower and rotate a sample dispensing arm 80 (refer to FIGS. 3 and 5) which is described later, drive circuit (not shown in the drawings) for actuating the stepping motor 80b, and a pump (not shown in the drawing) for suctioning and dispensing sample.

The reagent dispensing drive part 130a is provided with a stepping motor 130b that functions to raise, lower and rotate a reagent dispensing arm 130 (refer to FIGS. 3 and 5) which is described later, drive circuit (not shown in the drawings) for actuating the stepping motor 130b, and a pump (not shown in the drawing) for suctioning and dispensing reagent.

The first drive part 501 is provided with a first stepping motor (not shown in the drawing) that functions to rotate the first reagent table 11 which is described later, and a drive circuit (not shown in the drawing) for actuating the first stepping motor. The first reagent table 11 rotates an amount commensurate with the number of pulses of the drive pulse signals supplied from the controller 501 to the first drive part 502, then stops.

The second drive part 503 is provided with a second stepping motor (not shown in the drawing) that functions to rotate the second reagent table 12 (refer to FIG. 5), and a drive circuit (not shown in the drawing) for actuating the second stepping motor. The second reagent table 12 rotates an amount commensurate with the number of pulses of the drive pulse signals supplied from the controller 501 to the second drive part 503, then stops.

The controller 501 controls the rotational movement of each reagent table 11 and 12 by determining the amount of rotational movement from the origin positions of the reagent tables 11 and 12 by counting the number of pulses of the supplied drive pulse signals.

The sensor 51 functions to detect the lock status of the first cover 30 (refer to FIG. 3) which is described later, and to transmit a lock signal to the controller 501 when the first cover 30 is locked.

Similarly, the sensor 52 functions to detect the lock status of the second cover 40 (refer to FIG. 3) which is described later, and to transmit a lock signal to the controller 501 when the second cover 40 is locked.

The reagent barcode reader 350 functions to read each of the barcodes on the first reagent table 11 and second reagent table 12, and is disposed at a predetermined distance from the reagent storing part 6 in the vicinity of the side surface 21 of the reagent storing part 6 which is described later. The reagent barcode reader 350 is able to transmit and receive data to/from the controller 501, and has a drive circuit (not shown in the drawings) for controlling the ON/OFF condition of the reagent barcode reader 350. The position of the reagent barcode reader 350 is normally fixed.

The sample barcode reader 3c functions to read the barcode adhered to the test tube 250 that contains a sample and is loaded in the rack 251 that is transported by the transporting unit 3, and is provided opposite the rack 251 that is transported by the transporting unit 3 and in the vicinity of the aspirating position 2a of the previously mentioned measuring unit 2. The sample barcode reader 3c is able to transmit and receive data to/from the controller 501, and has a drive circuit (not shown in the drawings) for controlling the ON/OFF condition of the reagent barcode reader 3c. The position of the sample barcode reader 3c is normally fixed.

The first optical information obtaining part 90 and the second optical information obtaining part 140 (refer to FIGS. 3 and 5) function to obtain the optical information of samples, and are capable of transmitting and receiving data to/from the controller 501. The first optical information obtaining part 90 and the second optical information obtaining part 140 are described in detail later.

Figure 20:
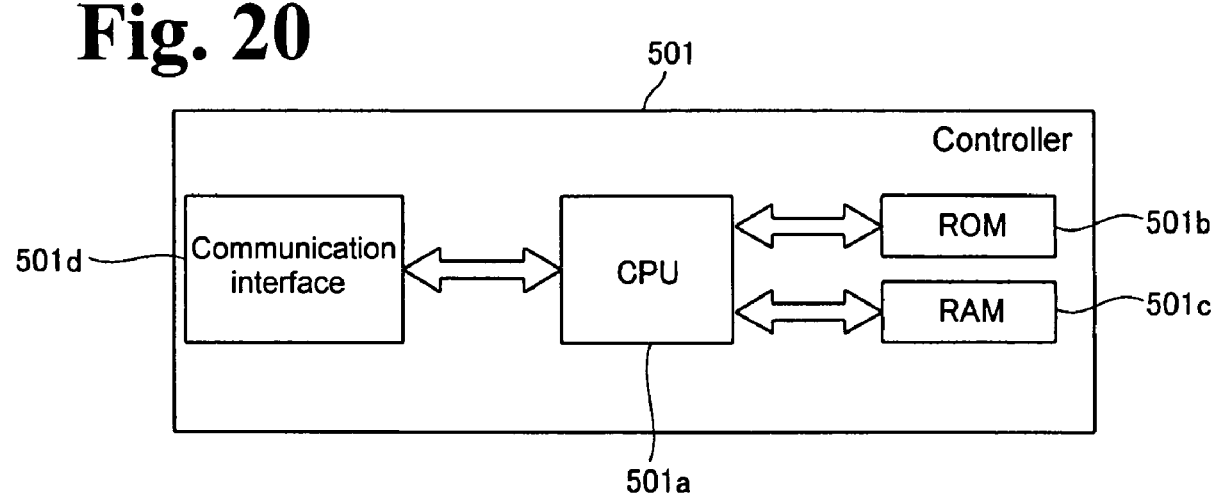
FIG. 20 is a block diagram of the measuring unit of the embodiment of the sample analyzer of the present invention.

As shown in FIG. 20, the controller 501 is mainly configured by a CPU 501a, ROM 501b, RAM 501c, and communication interface 501d.

The CPU 501a is capable of executing computer programs stored in the ROM 501b, and computer programs loaded in the RAM 501c. The ROM 501b stores the computer programs executed by the CPU 501a, and the data and the like used in the execution of the computer programs. The RAM 501c is used when reading the computer programs stored in the ROM 501b. The RAM 501c is further used as a work area of the CPU 501a when these computer programs are being executed.

The communication interface 501d is connected to the control unit 4, and functions to transmit sample optical information to the control unit 4 and receive signals from the control unit 4. The communication interface 501d further functions to transmit commands from the CPU 501a to drive the various parts of the transporting unit 3 and measuring unit 2.

As shown in FIG. 3, the measuring unit 2 includes a reagent storing part 6 and for storing reagent, and a reagent replacing part 7 for replacing or adding reagent.

Figure 4:
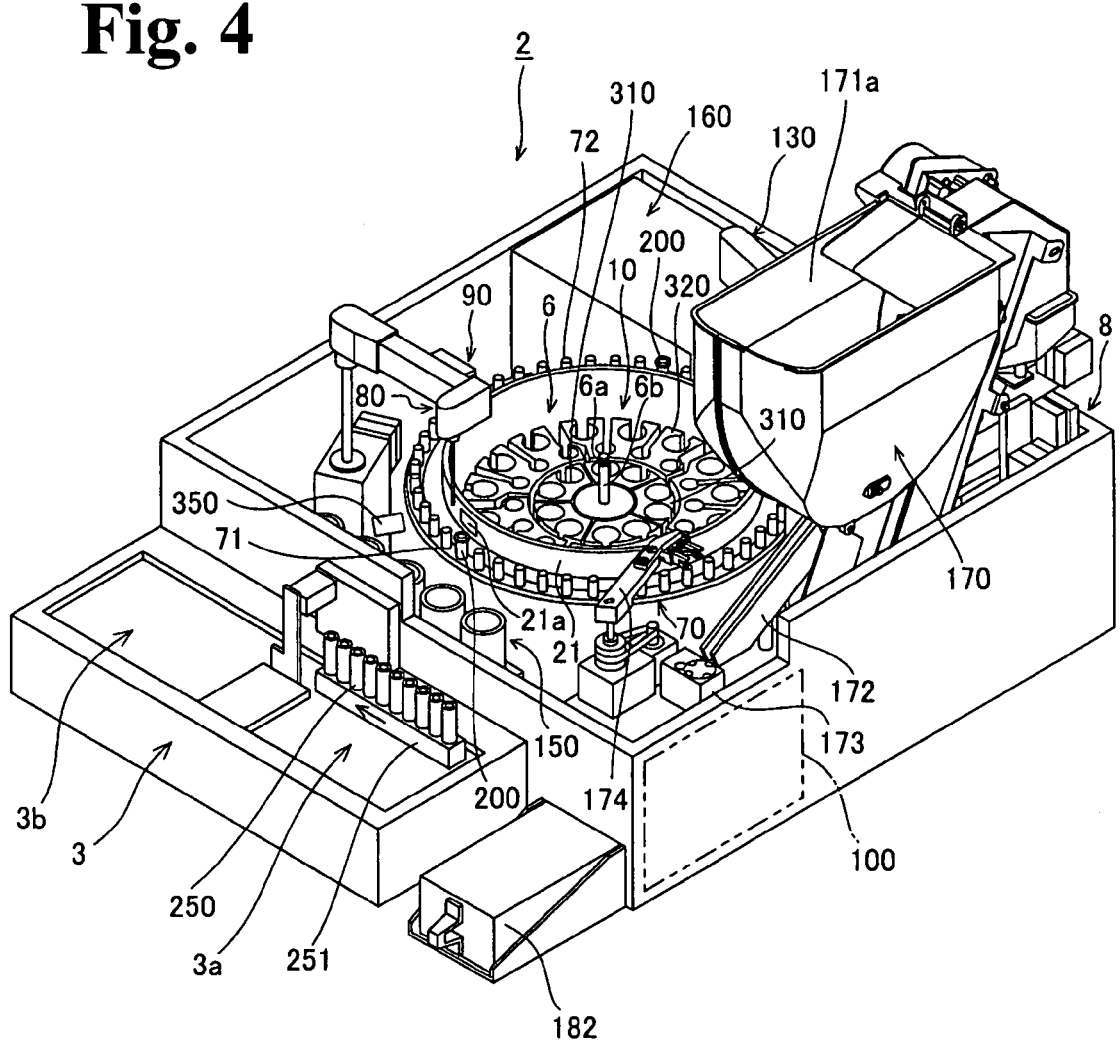
FIG. 4 is a perspective view showing the measuring unit and regent preserving section of the embodiment of the sample analyzer of the present invention.

The reagent storing part 6 is provided to store the reagent containers 300 that contained the reagent added to sample within the cuvette 200 at a low temperature (approximately 10 degrees Centigrade), and transport the reagent containers 300 in a rotary direction. Deterioration of the reagent is prevented by preserving the reagent at low temperature. As shown in FIGS. 3 through 5, the reagent storing part 6 includes a reagent transporting part 10 (refer to FIGS. 4 and 5) for holding and moving reagent rotationally, and an outer wall 20 (refer to FIG. 3) provided to cover the perimeter and top of the reagent transporting part 10. The reagent transporting part 10 that holds the reagent is disposed in a cooled region formed by the outer wall 20, first cover 30 and second cover 40 of the reagent replacing part 7 which is described later.

The reagent transporting part 10 includes a circular first reagent table 11, and annular second reagent table 12 which is disposed on the outer side of the circular first reagent table to as to be concentric therewith, as shown in FIG. 5. The first reagent table 11 and second reagent table 12 accommodate, so as to be removable, the first reagent container racks 310 and second reagent container racks 320 that hold the reagent containers 300. The outer wall 20 is configured by a side surface 21 (refer to FIG. 4), a top surface 22 that is fixedly attached to the side surface 21 (refer to FIG. 3), and a removable cover 23 (refer to FIG. 3). Furthermore, the barcode reader 350 is disposed at a predetermined distance from the reagent storing part 6 in the vicinity of the side surface 21 (refer to FIG. 4) of the reagent storing part 6.

The first reagent table 11 and second reagent table 12 are mutually and independently rotatable in both clockwise and counterclockwise directions. Thus, the first reagent container racks 310 and second reagent container racks 320 that hold the reagent containers 300 containing reagent are transported in a rotational direction by the first reagent table 11 and second reagent table 12. The reagent to be dispensed is able to thus be placed near the reagent dispensing arm 130 by transporting the reagent container 300 in a rotational direction when the reagent dispensing arm 130 is to dispense reagent in a manner described later.

A heat-insulating material (not shown in the drawing) is mounted on the side surface 21 of the outer wall 20 to prevent the cool air within the reagent storing part 6 (cooled region) from escaping. As shown in FIG. 4, a shutter 21a that is able to be opened and closed is provided at a position opposite the barcode reader 350 on the side surface 21 of the outer wall 20. The shutter 21a is configured so as to open only when the barcode reader 350 reads the barcode on the first reagent containers 310 and second reagent containers 320. Thus, the cool air within the reagent storing part 6 (cooled region) is prevented from escaping to the outside.

As shown in FIG. 3, the top surface 22 of the outer wall 20 includes three holes 22a, 22b, and 22c. Reagent stored in the reagent storing part 6 is aspirated by the reagent dispensing arm 130 through the three holes 22a, 22b, 22c. The hole 22a is positioned above the reagent container 300 held in the first reagent container rack 310. Reagent is aspirated from the reagent container 300 held in the first reagent container rack 310 through the hole 22a. The holes 22b and 22c are respectively positioned above the reagent containers 300 held in the front and the back row in the second reagent container table 320. Reagent is aspirated from the reagent containers 300 held in the front and the back row in the second reagent container table 320 through the holes 22b and 22c.

A semicircular opening is formed in the reagent storing part 6 (cooled region) by removing the cover 23 together with the first cover 30 and second cover 40. The first reagent container rack 310 and second reagent container rack 320 are able to be positioned in the reagent storing part 6 through this opening when starting the measurement performed in the sample analyzer 1.

Figure 15:
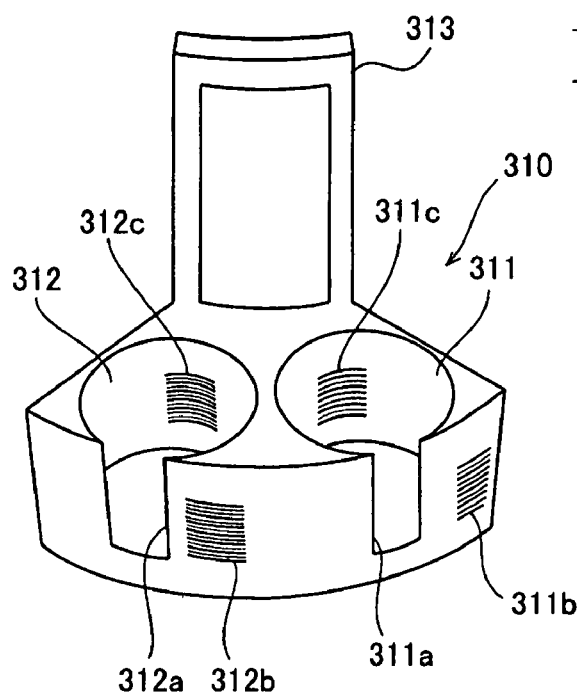
FIG. 15 is a perspective view of a first reagent container rack of the embodiment.
Figure 17:
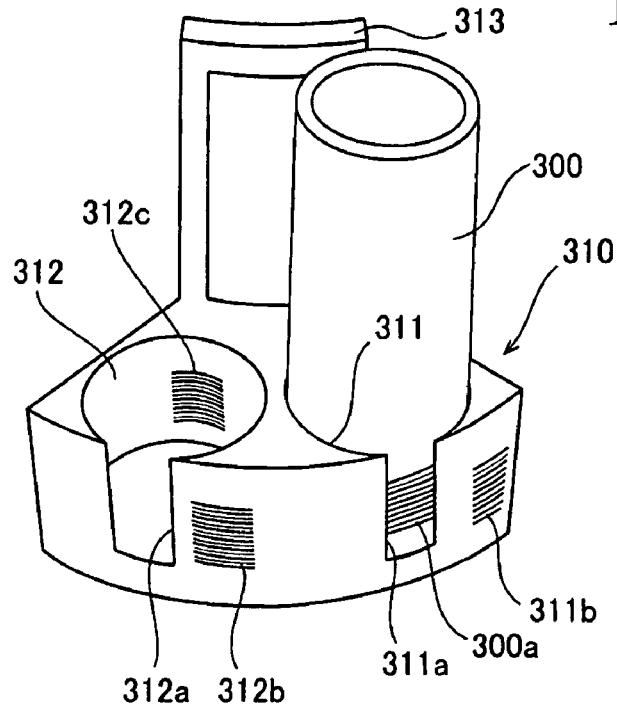
FIG. 17 is a perspective view of reagent container held in the first reagent container rack shown in FIG. 15.

As shown in FIG. 5, the first reagent container rack 310 has five positions on the first reagent table 11. The reagent containers 300 are disposed in a ring in the five reagent container racks 310. As shown in FIGS. 15 and 17, the first reagent container rack 310 includes two holders 311 and 312 for holding reagent containers 300, slots 311a and 312a respectively provided on the front side of the holders 311 and 312, and one handle 313 provided so as to project upward. As shown in FIG. 17, the holders 311 and 312 are round in shape when viewed on a plane, and are capable of holding the reagent container 300 when the cylindrical reagent container 300 is inserted. Reagent containers 300 that have an external diameter that is smaller than the internal diameter of the holders 311 and 312 are able to be held by the holders 311 and 312 by mounting an adapter (not shown in the drawing) in the holders 311 and 312. The first reagent container rack 310 further includes two types of racks formed to allow different combinations of internal diameters of the holders 311 and 312. A user may utilize reagent containers 300 of difference sizes by changing the type of rack. Barcodes 311b and 312b are provided on the front side of the outer surface of the holders 311 and 312, respectively, and barcodes 311c and 312c are provided on the inside surfaces of the holders 311 and 312, respectively.

The two holders 311 and 312 are able to hold one at a time a plurality of reagent containers 300 that contain various reagents to be added when preparing a measuring sample from a specimen. That is, ten (2×5=10) reagent containers 300 are able to be accommodated in the first reagent table 11. The slots 311a and 312a are provided to allow the barcode reader 350 to read the barcodes 311c and 312c, respectively. The handle 313 is held when removing the first reagent container rack 310 from the reagent storing part 6.

The barcodes 311b and 312b include position information for identifying the position of the holders 311 and 312, respectively. The barcodes 311c and 312c include information indicating the presence/absence of a reagent container 300 hold in the holders 311 and 312 (no reagent container information). The barcode 300a of the reagent container 300 includes information for specifying the attribute information (holder number, reagent name, reagent container type, lot number, reagent valid period and the like) of the reagent contained in the reagent container 300. That is, the holder number is basically specified in the barcode 300a of the reagent container 300 read by the barcode reader 350. That is, the reagent name, reagent container type, lot number, reagent valid period and the like are basically specified in the barcode 300a of the reagent container 300 read by the barcode reader 350.

When the holder 311 holds a reagent container 300, the barcode 300a of the reagent container 300 is read and the barcode 311c is not read. That is, when the barcode 300a is read after the barcode 311b has been read by the barcode reader 350, the controller 4a recognizes via the barcode reader 350 that a reagent possessing reagent information is held in the holder 311. Furthermore, when the barcode 311c is read after the barcode 311b has been read by the barcode reader 350, the controller 4a recognizes that a reagent is not held in the holder 311. When either the barcode 300a or barcode 311c is not read after the barcode 311b has been read by the barcode reader 350 (as when a reagent container 300 is oriented horizontally), the controller 4a recognizes a reading error and a reading error message is displayed on the display 4b.

Figure 16:
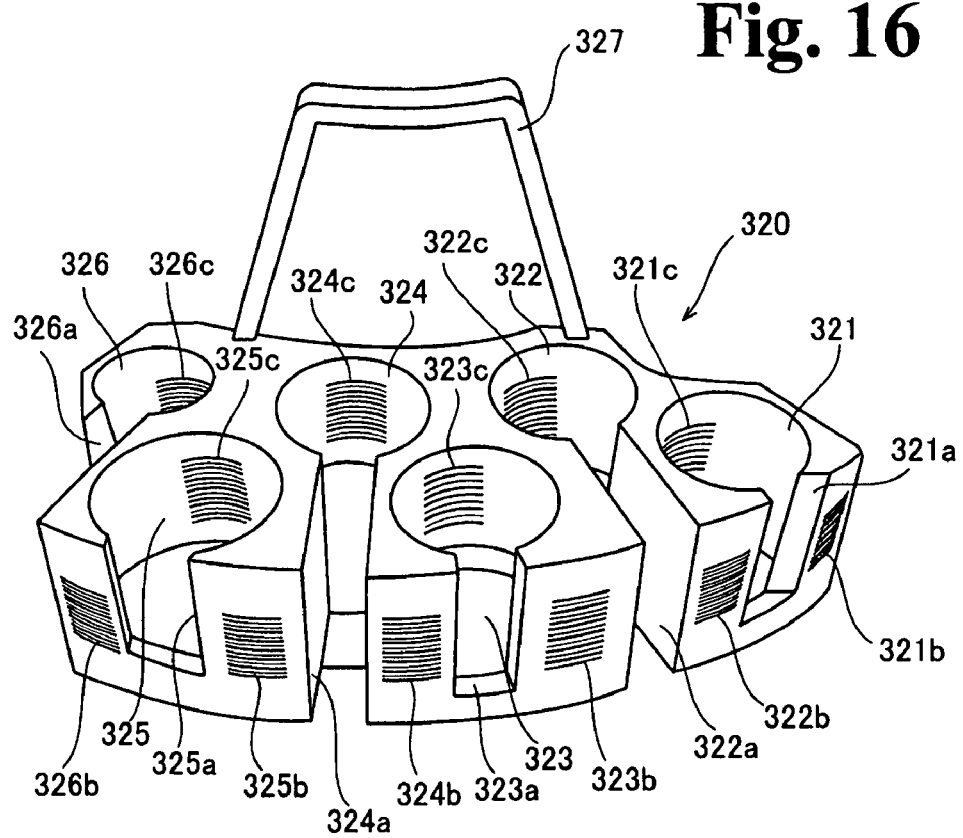
FIG. 16 is a perspective view of a second reagent container rack of the embodiment.
Figure 18:
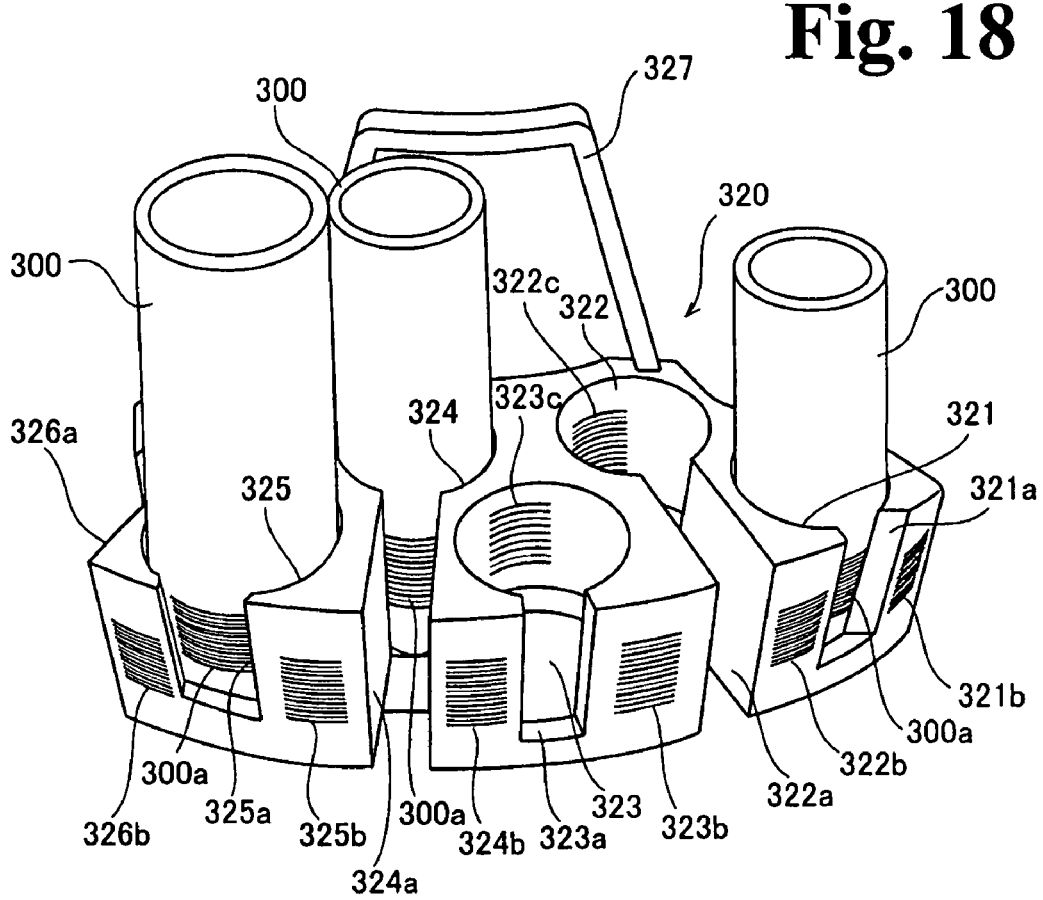
FIG. 18 is a perspective view of reagent containers held in the second reagent container rack shown in FIG. 16.

As shown in FIG. 5, the five second reagent container racks 320 are able to be accommodated in the second reagent table 12. The reagent containers 300 are disposed in a ring in the five reagent container racks 320. One location among the gaps between the five places of the mutually adjacent second reagent container racks 320 has a space larger than the spaces of the other four locations. The barcodes 311b and 312b of the first reagent container rack 310 disposed on the first reagent table 11 positioned within the second reagent table 2, and the barcode 300a of the reagent container 300 held by the first reagent rack 310 is able to be read by the barcode reader 350 positioned on the outside of the reagent storing part 6 through the large-space gap 12a. as shown in FIGS. 16 and 18, the second reagent container rack 320 includes six holders 321 through 326 for holding reagent containers 300, slots 321a through 326a respectively provided on the front side of the holders 321 through 326, and one handle 327 provided so as to project upward. The holders 321 through 326 of the second reagent container rack 320 is circular, and capable of holding cylindrical reagent containers 300 inserted therein, similar to the first reagent container rack 310. The second reagent container rack 320 includes three types of racks formed so as to have respectively different combinations of internal diameters among the holders 321 through 326. The second reagent container rack 320 is capable of accommodating the same reagents as those accommodated in the first reagent container rack 310.

Barcodes 321b and 322b are provided on both sides of the front row slot 321a. Similarly, the barcodes 323b and 324b and barcodes 325b and 326b are respectively provided on both sides of slot 323a and slot 325a. The barcodes 321c through 326c are respectively provided on the inside surface of the holders 321 through 326.

The barcodes 321b through 326b include position information for identifying the position of the holders 321 through 326. The barcodes 321c and 326c include information indicating the presence/absence of a reagent container 300 hold in the holders 321 through 326 (no reagent container information).

The reagent information and no reagent container information read by the barcode reader 350 are stored on the hard disk 401d by the controller 4a with the corresponding position information. The information stored on the hard disk 401d is displayed on the reagent placement screen 410 on the display 4b via the controller 4a of the control unit 4.

The barcodes 311b, 312b, and 321b through 326b display four-unit values. The first column has a value of either [A] or [B]; the value [A] indicates the reagent container 300 is disposed on the second reagent table 12, and the value [B] indicates the reagent container 300 is disposed on the first reagent table 11. The second column has a value of [1] to [5]; the values [1] through [3] respectively indicate the three shape types of the second reagent container rack 320, and the values [4] and [5] indicate the two shape types of the first reagent container rack 310. The third column has a value of [0] to [9] indicating the number of the first reagent container rack 310 or second reagent container rack 320. In the barcodes 311b and 312b of the first reagent container rack 310, the fourth column has a value of either [1] or [2]; the values [1] and [2] respectively indicate the holder 311 and 312. In the barcodes 321b and 326b of the second reagent container rack 320, the fourth column has a value of [1] to [6]; the values [1] through [6] respectively indicate the holders 321 through 326. The barcode values (barcodes 311b, 312b, and 321b through 326b) are displayed in the position display area 421a or 422a of the reagent display region (first reagent display region 421 or second reagent display region 422) of the reagent placement screen 410, as shown in FIG. 7. For example, a barcode value [A15-6] represents the rack corresponds type [1] among the three types of racks that are able to be accepted in the second reagent table 12 (second reagent container rack 320), in the sixth holder (holder 326) of the fifth rack of the second reagent container racks 320.

The reagent name and no reagent container information among the attribute information are displayed in the reagent name display area 421b and 422b of the first reagent display region 421 and the second reagent display region 422 in the reagent placement screen 410. As shown in FIG. 7, the reagent name is displayed in the reagent name display area 421b or 422b when a reagent is placed, and nothing is displayed in the reagent name area 421b or 422b when a reagent is not placed. In FIG. 7, for example, the reagent name [PT-TPC+] is placed at reagent position [A15-6], and no reagent id placed at the reagent position [A28-1]. Since the barcode reader 350 does not read a barcode when the reagent container rack itself is not placed, nothing is displayed in the first reagent display area 421 or second reagent display area 422 corresponding to the region of the missing first reagent container rack 310 or the second reagent container rack 320.

Figure 13:
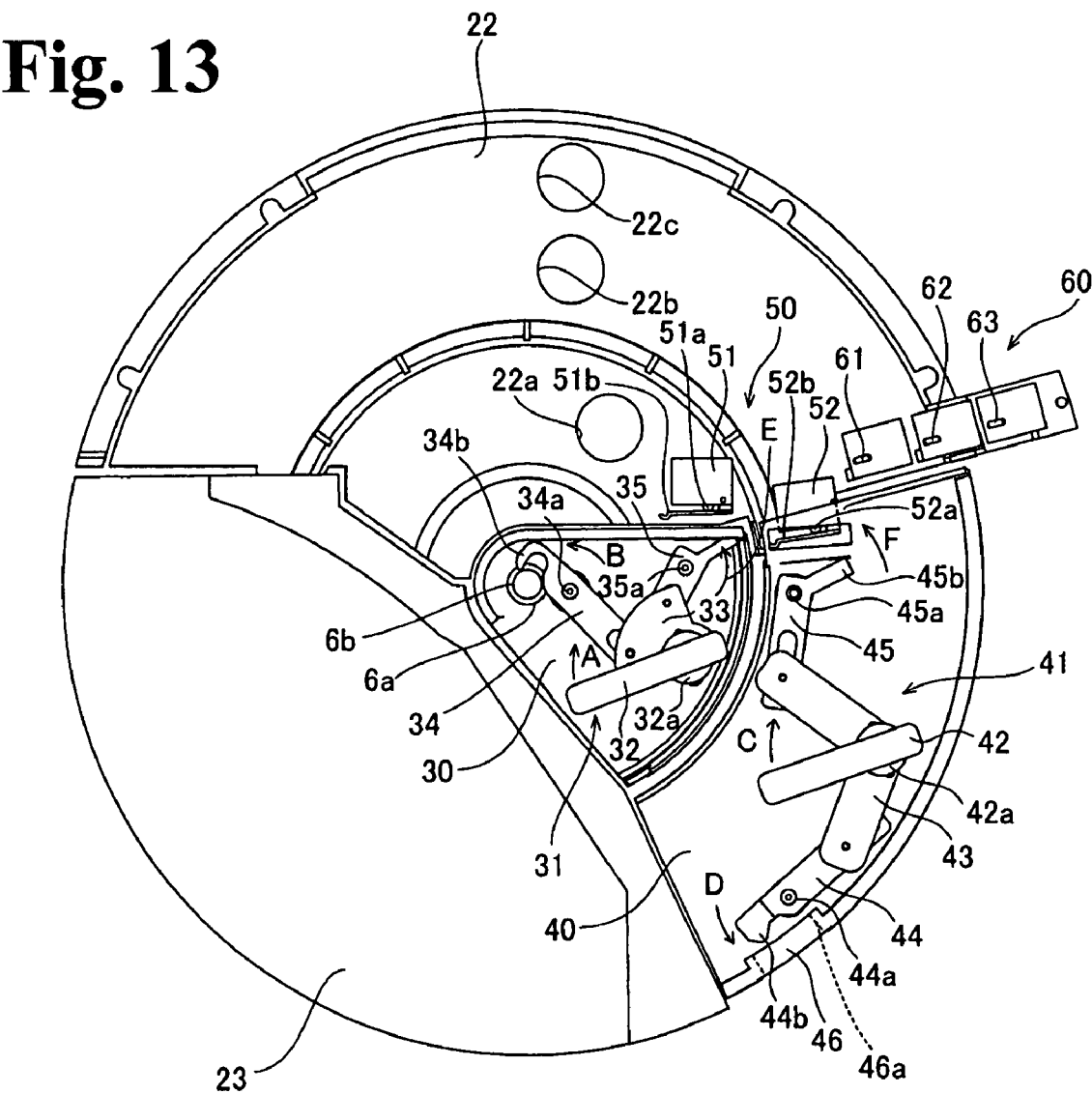
FIG. 13 shows the first cover part and second cover part in a locked condition on the reagent replacement section shown in FIG. 8.
Figure 14:
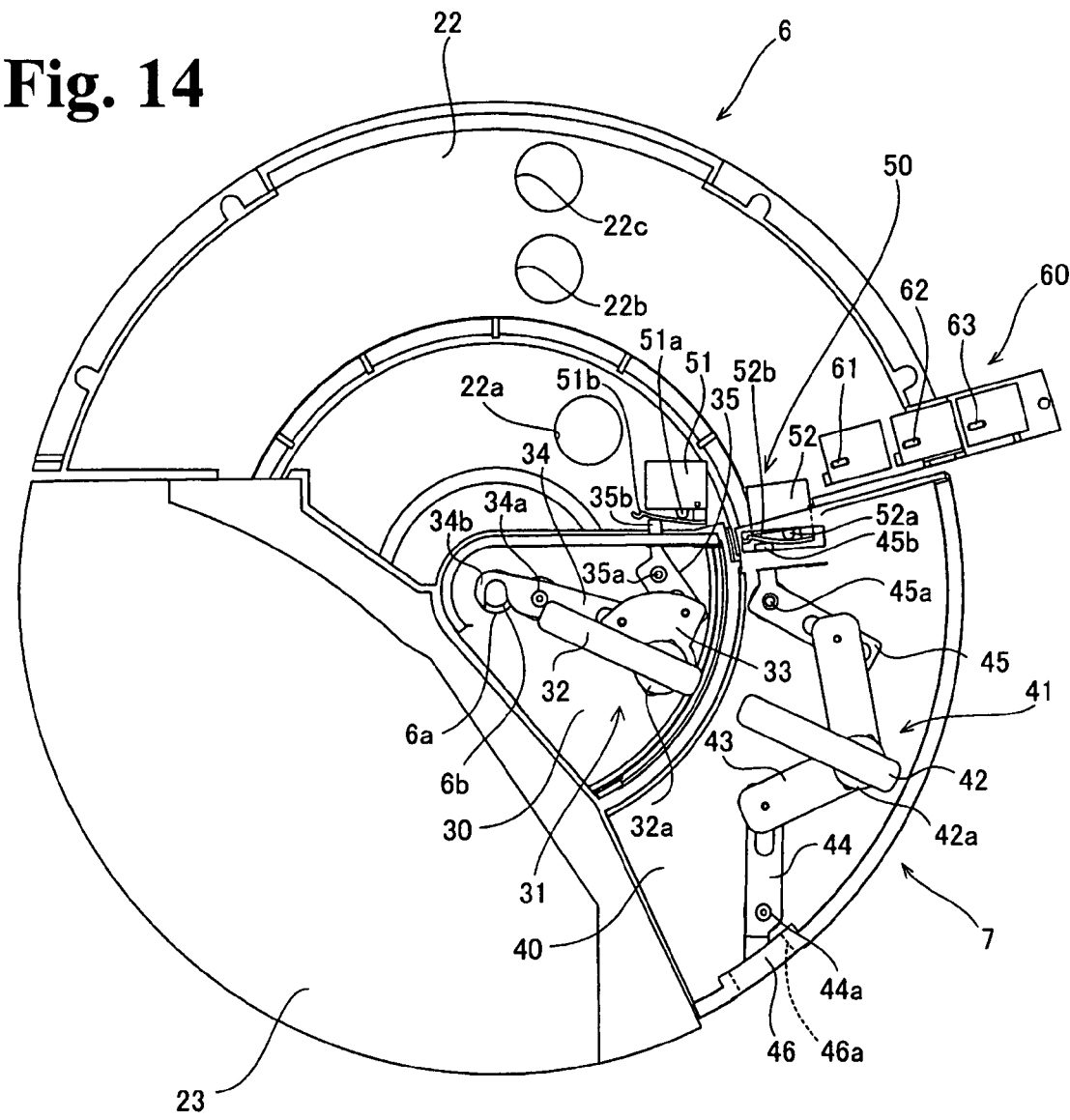
FIG. 14 shows the first cover part and second cover part in an unlocked condition on the reagent replacement section shown in FIG. 8.

The reagent replacing part 7 is provided near the center of the sample analyzer 1, as shown in FIGS. 1 and 2. In the present embodiment, the reagent replacing part 7 includes a first cover 30 and second cover 40 respectively provided for the locking devices 31 and 41 so as to be removable, sensor 50 (refer to FIGS. 13 and 14) for detecting the lock status of the first cover 30 and second cover 40, and an indicator 60 for alerting a user to the transport status of the first reagent table 11 and second reagent table 12, as shown in FIGS. 8 through 14. The unlocked condition of the of the locking device 31 of the locking device 30 and the locking device 41 of the second cover 40 are shown in FIG. 13, and the locked condition of the locking device 31 of the first cover 30 and the locking device 41 of the second cover 40 are shown in FIG. 14.

Figure 8:
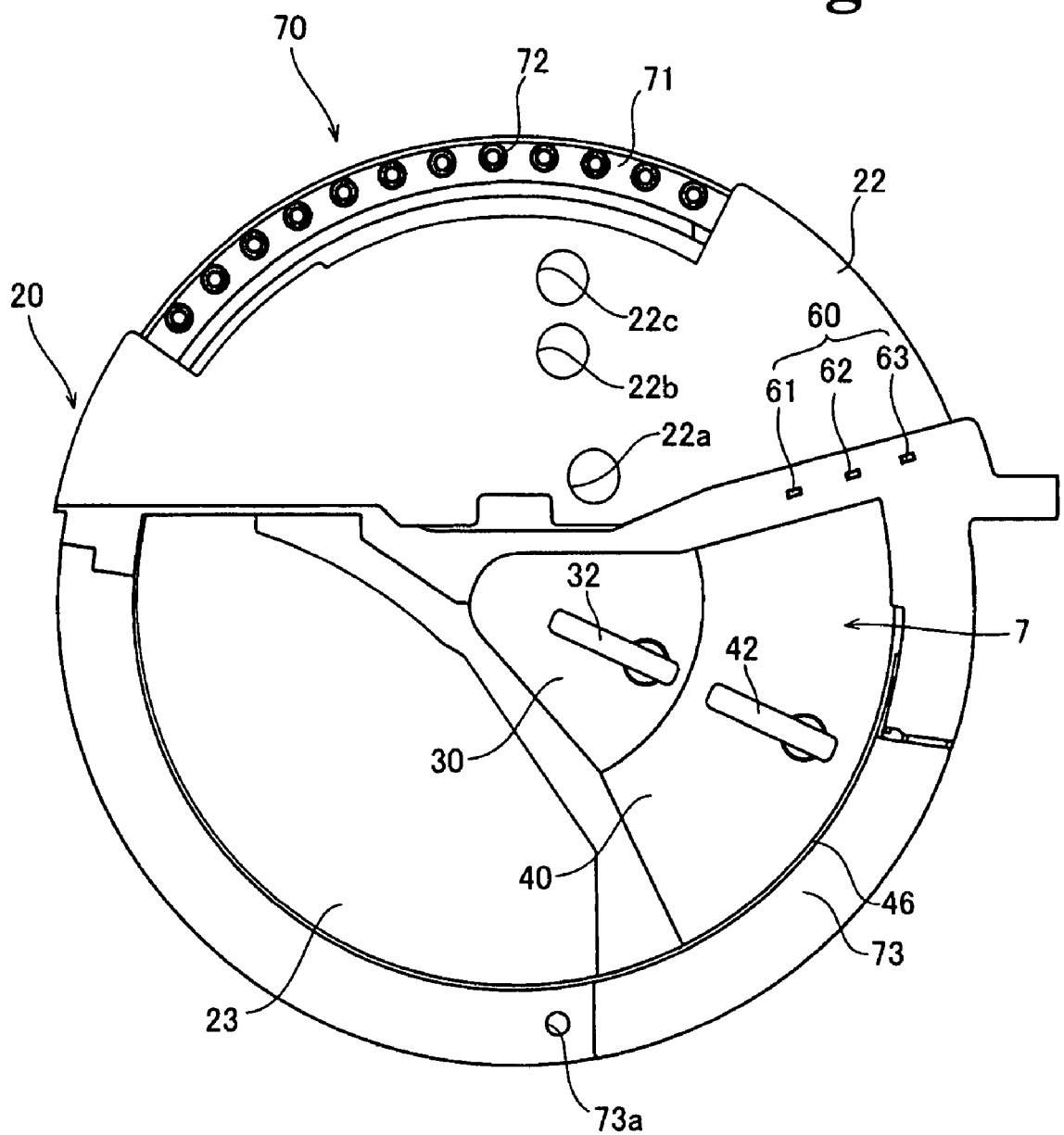
FIG. 8 is a top view of the reagent preserving section, reagent replacement section, cuvette transporting section, first cover part, and second cover part of the embodiment of the sample analyzer of the present invention.
Figure 11:
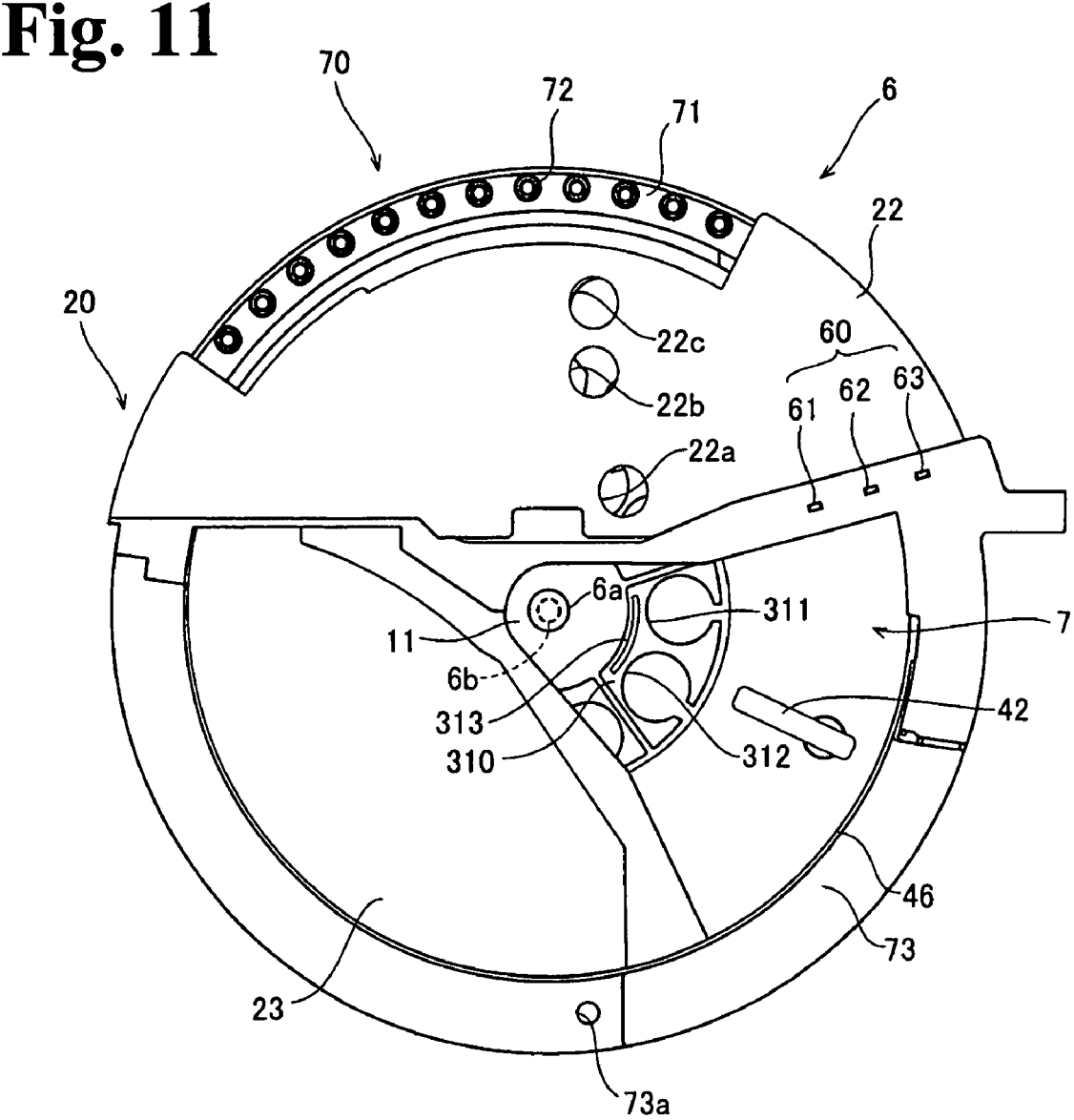
FIG. 11 is a top view of the first cover part removed from the state shown in FIG. 8.

The first cover 30 is able to be removed when replacing the reagent containers 300 placed to the first reagent table 11 (first reagent container rack 310), as shown in FIGS. 8 and 11. The first cover 30 has a fan-like configuration and is mounted above the first reagent table 11. The size and shape of the first cover 30 allow only a single first reagent container rack 310 to be removed when the first cover 30 has been removed. As shown in FIGS. 13 and 14, the locking device 31 of the first cover 30 is provided to lock the first cover 30 during normal use or after reagent replacement or addition has been completed, and is provided so that the controller 4a is aware when reagent replacement or addition has been completed in the first reagent table 11.

Figure 9:
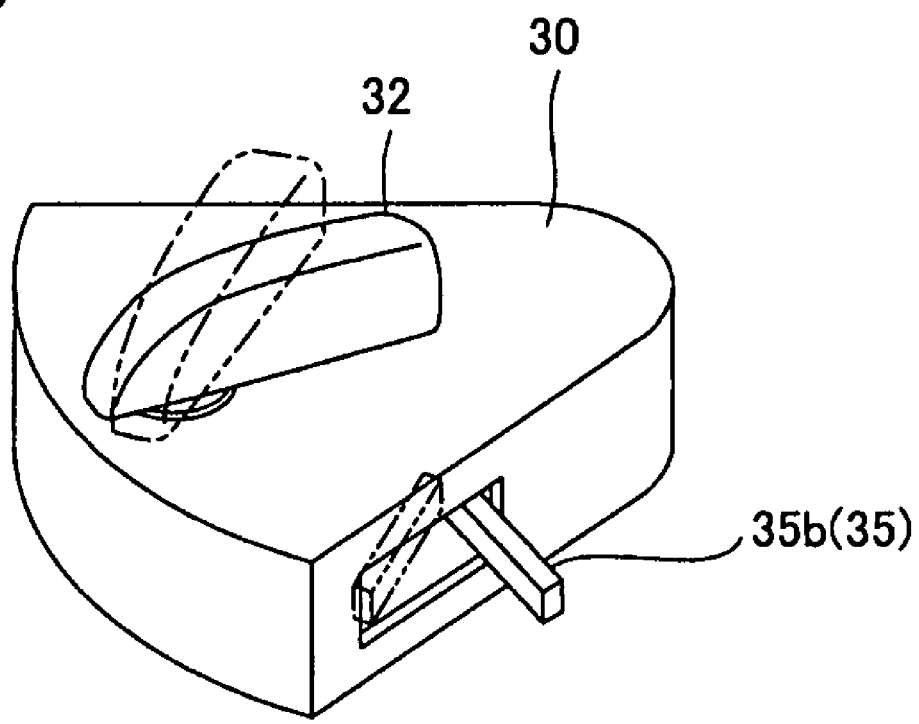
FIG. 9 is a perspective view showing the first cover part of the embodiment of the sample analyzer of the present invention.

As shown in FIGS. 9, 13, and 14, the locking device 31 of the first cover 30 is configured by a handle 32 that is rotatable by a user so as to pivot on a rotating shaft 32a, relay member 33 for integratedly rotating the handle 32 to pivot on the rotating shaft 32a, locking member 34 capable of engaging with the relay member 33 and rotating on a rotating shaft 34a, and lock sensing member 35 for engaging the relay member 33 and rotating on a rotating shaft 35a. The locking member 34 is provided with a hook 34b on the end on the opposite side from the relay member 33. The locking member 35 is provided, at the end on the opposite side from the relay member 33, with a pressing piece 35b (refer to FIG. 9) for pressing a microswitch 51a of a sensor 50 when the cover 30 is locked. As shown in FIGS. 11, 13, and 14, a cylindrical connector 6a is fixedly mounted to the center of the reagent storing part 6, and connects to the hook 34b of the hook member 34. The outer diameter of the cylindrical connector 6a is greater than the inner diameter of the hook 34b. A channel 6b having an outer diameter substantially the same as the inner diameter of the hook 34 is provided at a position corresponding to the hook 34b of the cylindrical connector 6a.

When the handle 32 is rotated in the arrow A direction on the rotating shaft 32a from the unlocked state shown in FIG. 13, the relay member 33 is also rotated in the arrow A direction on the rotating shaft 32a. Since the hook member 34 engages the relay member 33, the hook member 34 is rotated in the arrow B direction on the rotating shaft 34a in conjunction with the rotation of the relay member 33 in the arrow A direction. Therefore, the hook 34b of the hook member 34 engages the channel 6b of the cylindrical connecting part 6a and becomes locked.

When a user attempts to remove the first cover 30 in the locked state, removal of the first cover 30 is prevented by the engagement of the hook 34b of the hook member 34 in the channel 6b of the connector 6a.

Figure 12:
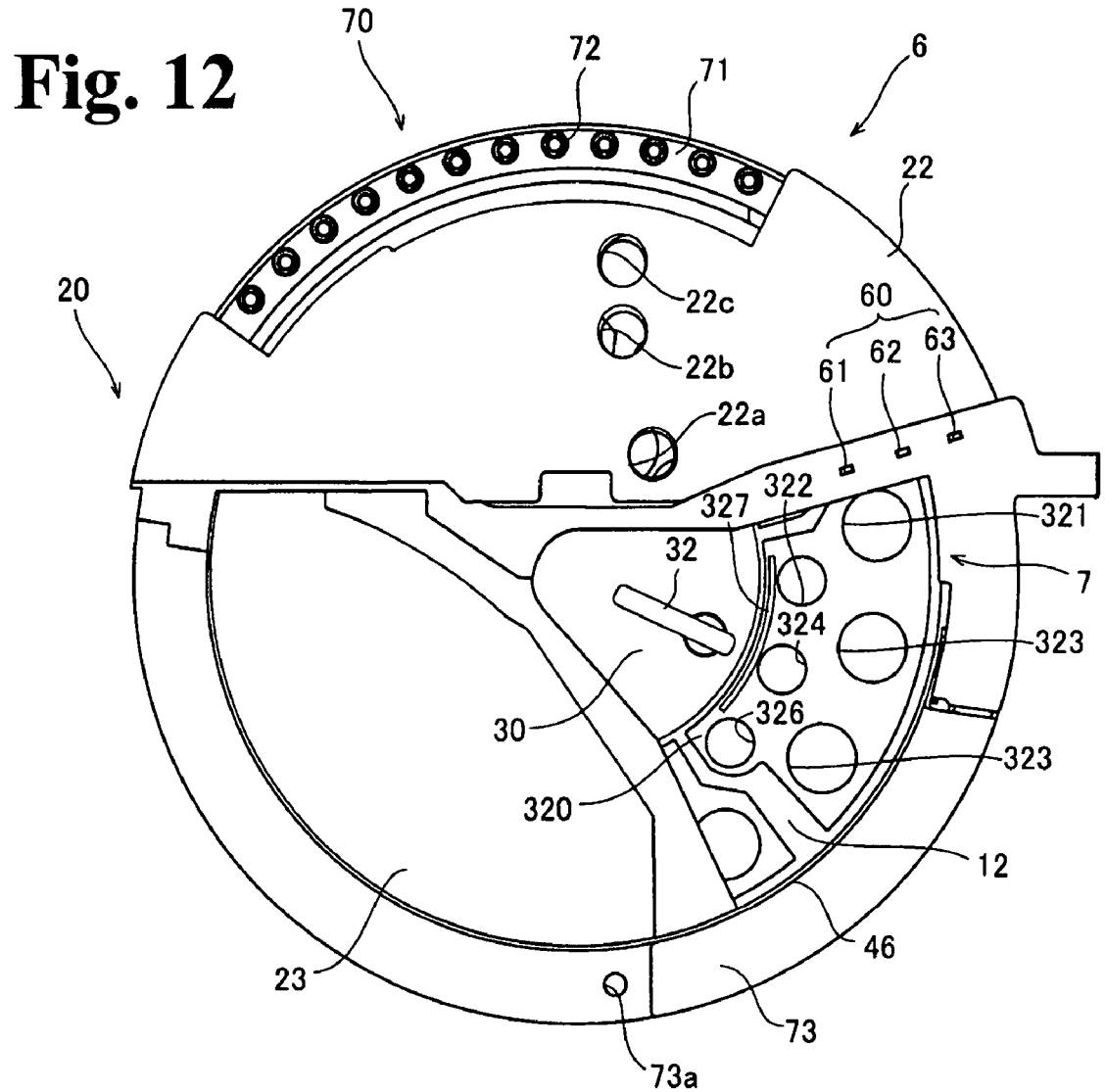
FIG. 12 is a top view of the second cover part removed from the state shown in FIG. 8.

As shown in FIGS. 8 and 12, the second cover 40 is able to be removed when replacing a reagent container 300 placed on the second reagent table 12 (second reagent container rack 320). The second cover 40 is mounted above the second reagent table 12 on the outer side of the first cover 30. The size and shape of the second cover 40 allow only a single second reagent container rack 320 to be removed when the second cover 40 has been removed. As shown in FIGS. 13 and 14, the locking device 41 of the second cover 40 is provided to lock the second cover 40 during normal use or after reagent replacement or addition has been completed, and is provided so that the controller 4a is aware when reagent replacement or addition has been completed in the second reagent table 12.

Figure 10:
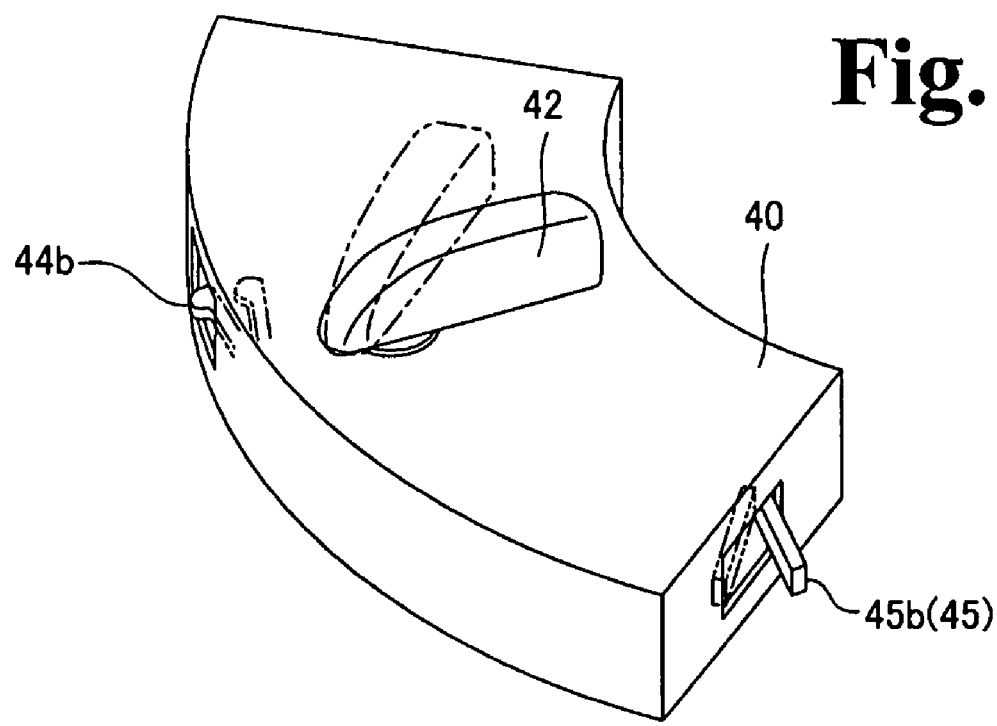
FIG. 10 is a perspective view showing the second cover part of the embodiment of the sample analyzer of the present invention.

As shown in FIGS. 10, 13, and 14, the locking device 41 of the second cover 40 is configured by a handle 42 that is rotatable by a user so as to pivot on a rotating shaft 42a, bifurcated relay member 43 for integratedly rotating the handle 42 to pivot on the rotating shaft 42a, locking member 44 capable of engaging with the relay member 43 and rotating on a rotating shaft 44a, and lock sensing member 45 for engaging the relay member 43 and rotating on a rotating shaft 45a. The locking member 44 is provided with a convex lock 44b on the end opposite from the relay member 43 (refer to FIG. 10). The locking member 45 is provided, at the end on the opposite side from the relay member 43, with a pressing piece 45b (refer to FIG. 10) for pressing a microswitch 52a of a sensor 50 when the cover 40 is locked. A second cover mount 46 attached to the second cover 40 (refer to FIGS. 13 and 14) is provided, a position corresponding to the lock 44b, with a connector hole 46a for connecting with the lock 44b.

When the handle 42 is rotated in the arrow C direction on the rotating shaft 42a from the unlocked state shown in FIG. 13, the relay member 43 is also rotated in the arrow C direction on the rotating shaft 42a. Since the hook member 44 engages the relay member 43, the hook member 44 is rotated in the arrow D direction on the rotating shaft 44a in conjunction with the rotation of the relay member 43 in the arrow C direction. Therefore, the hook 44b of the hook member 44 engages the connector hook 46a of the second cover mount 46 and becomes locked.

When a user attempts to remove the first cover 40 in the locked state, removal of the first cover 40 is prevented by the engagement of the hook 44b of the hook member 44 in the connector hole 46a of the second cover mount 46.

The sensor 50 includes a first sensor 51 and second sensor 52 for respectively detecting the locked state of the first cover 30 and second cover 40. The first sensor 51 includes a microswitch 51a, and flat spring 51b. The second sensor 52 includes a microswitch 52a, and a flat spring 52b.

The first sensor 51 is configured such that the microswitch 51a detects the locked state of the first cover 30 when the flat spring 51b is pressed by the pressing piece 35b of the locking device 31 of the first cover 30, as shown in FIGS. 13 and 14. Specifically, the lock detecting member 35, which is engaged with the relay member 33, is rotated in the arrow E direction on the rotating shaft 35a by the relay member 33 which is rotated in the arrow A direction together with the handle 32 when the first cover 30 is being locked. Therefore, the microswitch 51a is pressed by the flat spring 51b of the first sensor 51 since the flat spring 51b of the first sensor 51 is engaged when the pressing piece 35b of the lock sensing member 35 is rotated in the arrow E direction. The locked condition of the first cover 30 is detected by the first sensor 51 since the lock 34b of the locking device 31 is engaged with the cylindrical connector 6a while in this condition. The first sensor 51 transmits a signal to the controller 4a that indicates the first cover 30 is locked when the locked status of the first cover 30 has been detected.

Similarly, the second sensor 52 is configured such that the microswitch 52a detects the locked state of the second cover 40 when the flat spring 52b is pressed by the pressing piece 45b of the locking device 41 of the second cover 40. Specifically, the lock detecting member 45, which is engaged with the relay member 43, is rotated in the arrow F direction on the rotating shaft 45a by the relay member 43 which is rotated in the arrow C direction together with the handle 42 when the second cover 40 is being locked. Therefore, the microswitch 52a is pressed by the flat spring 52b of the second sensor 52 since the flat spring 52b of the second sensor 52 is engaged when the pressing piece 45b of the lock sensing member 45 is rotated in the arrow F direction. The locked condition of the second cover 40 is detected by the second sensor 52 since the lock 44b of the locking device 41 is engaged with the connector hole 46a of the second cover mount 46 while in this condition. The second sensor 52 transmits a signal to the controller 4a that indicates the second cover 40 is locked when the locked status of the second cover 40 has been detected.

The indicator 60 includes three LED indicators 61, 62, and 63. As shown in FIGS. 1 and 3, the three LED indicators 61, 62, and 63 are arranged in a row at predetermined distance in the vicinity of the second cover 40, and are visible to a user from outside the sample analyzer 1. The LED indicators 61, 62, and 63 are capable of emitting blue light or red light.

The LED indicator 61 functions to alert the user that the first reagent container rack 310 corresponding to the reagent on the first reagent table 11 specified by the user on the reagent placement screen 410 has been moved to the pick up position at which the reagent is able to be replaced (below the first cover 30). Specifically, the LED indicator 61 emits a red light during the rotation of the first reagent table 11, and emits a blue light when the first reagent container rack 310 corresponding to the specified reagent on the first reagent table 11 has moved to the pick up position and stopped. Thus, the user is alerted to the timing with which to remove the first cover 30 in order to add or replace the reagent.

The LED indicator 62 functions to alert the user that the second reagent container rack 320 corresponding to the reagent on the second reagent table 12 specified by the user on the reagent placement screen 410 has been moved to the pick up position at which the reagent is able to be replaced (below the second cover 40). Specifically, the LED indicator 62 emits a red light during the rotation of the second reagent table 12, and emits a blue light when the second reagent container rack 320 corresponding to the specified reagent on the second reagent table 12 has moved to the pick up position and stopped, similar to the LED indicator 61.

The LED indicator 63 functions to alert the user of the operating status of the cuvette moving table 71 which is described later. That is, when measuring a predetermined substance, the LED indicator 63 alerts the user of the timing by which to remove the cover 73 (refer to FIG. 8) positioned above the cuvette moving table 71 in order to add or replace a special cuvette (not shown in the drawing) on the cuvette moving table 71. The LED indicator 63 emits a red light while the cuvette moving table 71 is rotating, and emits a blue light when the cuvette moving table 71 has stopped.

In the present embodiment, when the user locks the first cover 30 or second cover 40 after replacing or adding reagent, the sample analyzer I automatically reads the barcode 300a of all reagent containers 300 held in the first reagent container racks 310 or second reagent container racks 320 that hold replaced reagent. Therefore, when, for example, a single reagent has been specified a command has been issued to replace the reagent, post replacement reagent placement is accurately displayed on the reagent placement screen 410 as if reagent other than the specified reagent has been replaced in the first reagent container rack 310 or second reagent container rack 320 in addition to the specified reagent.

As shown in FIGS. 3 through 5, the measuring unit 2 is provided with a cuvette moving section 7, sample dispensing arm 80, first optical information obtainer 90, lamp unit 100, heater 110, cuvette moving section 120, reagent dispensing arm 130, second optical information obtainer 140, urgent sample section 150, fluid flow section 160, and cuvette supplying device 170.

The cuvette moving section 170 functions to transport the cuvettes 20 to the various parts of the sample analyzer 1. The cuvette moving section 170 is configured by an annular cuvette moving table 71 disposed outside the annular second reagent table 12, a plurality of cylindrical cuvette holders 72 provided at predetermined intervals along the circumference of the cuvette moving table 71, and a cover 73 provided above the cuvette moving table 71 (refer to FIG. 8). The cuvette holders 72 are provided to each hold a single cuvette 200. The cover 73 is provided with a hole 73a through which reagent is dispensed to the cuvette 200 by the reagent dispensing arm 80 which is described later. A measurement sample is prepared by dispensing the reagent stored in the reagent storing part 6 and sample contained in the test tube 250 of the transporting unit 3 to the cuvette 200 held by the cuvette holder 72 of the cuvette moving table 71 (refer to FIG. 5).

The sample dispensing arm 80 functions to aspirate sample contained in the test tube 250 transported to the aspirating position 2a by the transporting unit 3, and dispense the aspirated sample through the hole 73a into the cuvette 200 held by the cuvette holder 72 of the cuvette moving table 71.

The first optical information acquiring section 90 is configured so as to acquire optical information from a specimen in order to measure the presence and concentration of interference substances (hemoglobin, bilirubin, chyle) in the specimen before adding reagent. Specifically, the presence and concentrations of interference substances are measured using four types of light (405 nm, 575 nm, 660 nm, 800 nm) among five types of light (340 nm, 405 nm, 575 nm, 660 nm, 800 nm) emitted from the lamp unit 100 which is described later. The 405 nm wavelength light is absorbed by chyle, hemoglobin, and bilirubin. That is, chyle, hemoglobin, and bilirubin influence the optical information measured using light at a wavelength of 405 nm. Furthermore, light at a wavelength of 575 nm is absorbed by chyle and hemoglobin, although essentially is not absorbed by bilirubin. That is, chyle and hemoglobin influence the optical information measured using light at a wavelength of 575 nm. Light at wavelengths of 660 nm and 800 nm are absorbed by chyle, although essentially are not absorbed by bilirubin and hemoglobin. That is, chyle influences the optical information measured using light at wavelengths of 660 nm and 800 nm. Chyle absorbs light from the low wavelength region 405 nm to the high wavelength region 800 nm, with chyle absorbing more light at the 660 nm wavelength than at the 800 nm wavelength. That is, the optical information measured using light at the 800 nm wavelength is less influenced by chyle than optical information at the 660 nm wavelength.

The acquisition of sample optical information by the first optical information obtainer 90 is performed before optically measuring (main measurement) the sample by the second optical information obtainer 140. The first optical information obtainer 90 obtains optical information from the sample within the cuvette 200 held by the holder 72 of the cuvette moving table 71.

The first optical information obtainer 90 is electrically connected to the controller 4a of the control unit 4, and transmits data (optical information) obtained by the first optical information obtainer 90 to the controller 4a of the control unit 4. Thus, in the control unit 4, the light absorbance of the sample within the cuvette 200 is determined relative to the five kinds of light emitted from a beam splitter optical fiber 101, and the presence and concentrations of interference substances in the sample are analyzed by performing data analysis of the data from the first optical information obtainer 90. In the present embodiment, a determination is made as to whether or not to analyze optical information acquired by the second optical information obtainer 140 based on the presence and concentrations of interference substances in the sample.

The lamp unit 100 is provided to supply light of five wavelengths (340 nm, 405 nm, 575 nm, 660 nm, 800 nm) to be used for the optical measurements performed by the first optical information obtainer 90 and the second optical information obtainer 140, as shown in FIG. 5. That is, a single lamp unit 100 is configured so as to be used jointly by the first optical information obtainer 90 and second optical information obtainer 140. The light of the lamp unit 100 is supplied to the first optical information obtainer 90 and the second optical information obtainer 140 by the beam splitter optical fiber 101 and beam splitter optical fiber 102, respectively.

The heater 110 is an incubation plate 111, and is provided with ten concave cuvette holders 111a. The cuvette holders 111a are each capable of holding a single cuvette 200, and function heat the sample within the cuvette 200 to approximately 37 degrees Centigrade by holding the cuvette 200 containing the dispensed sample for several minutes in the cuvette holder 111a. After the sample has been heated by the heater 110, reagent dispensing and measuring are performed within a set time. Thus, deterioration of the sample and the measurement sample prepared from the sample and reagent is prevented, and measurement results are stabilized.

The cuvette moving section 120 is provided to move the cuvettes 200 among the cuvette moving section 70, heater 110, and second optical information obtainer 140. The cuvette moving section 120 includes a catcher 121 for holding the cuvette 200, and a drive part 122 for moving the catcher 121. The catcher 121 is movable within a moving range 120a by means of the drive force of the drive part 122, and moves the cuvette 200 among the cuvette moving section 70, heater 110, and the measurement feeder 141 second optical information obtainer 140. The catcher 121 is provided with an oscillating function so as to be capable of agitating the reagent and sample within the cuvette 200 by oscillating the cuvette 200 while the cuvette 200 is held in the catcher 121.

The reagent dispensing arm 130 is provided to mix the reagent in the sample within the cuvette 200 by dispensing the reagent within the reagent container 300 placed in the reagent storing part 6 to the cuvette 200, as shown in FIGS. 3 through 5. Specifically, reagent is aspirated through either the hole 22a, 22b, or 22c of the outer wall 20 of the reagent storing part 6, the cuvette 200 is heated (37 degrees Centigrade), then removed from the cuvette holder 111a of the heater 110 and held by the catcher 121, whereupon the aspirated reagent is dispensed to the cuvette 200. The pipette part of the reagent dispensing arm 130 is provided with a heating function, and heats the aspirated reagent momentarily to approximately 37 degrees Centigrade. That is, the reagent, which has been stored at low temperature (approximately 10 degrees Centigrade) in the reagent storing part 6, is heated to approximately 37 degrees Centigrade by the reagent dispensing arm 130, and then is mixed with the sample which has also been heated to 37 degrees Centigrade. Thus, a measuring sample is prepared by adding reagent to a sample that has already been optically measured by the first optical information obtainer 90.

In the present embodiment, when reagent replacement is instructed during the operation of the reagent dispensing arm 130 and the dispensing operation of the dispensing reagent is being performed from the reagent table holding the specified reagent, the dispensing operation of the dispensing reagent by the reagent dispensing arm 130 from the reagent table that holds the specified reagent is suspended. In this case, when the dispensing reagent is accommodated on another reagent table as well which is different from the reagent table holding the specified reagent, the reagent dispensing arm 130 suspends the dispensing operation of the dispensing reagent from the table holding the specified reagent, and does not suspend the dispensing operation of the dispensing reagent hold on the other reagent table. When the dispensing reagent is only placed to the reagent table that holds the reagent specified for replacement, the reagent dispensing arm 130 stops the dispensing operation after completing the dispensing operation of the dispensing reagent to the sample being heated by the heater 110 and the sample already dispensed when reagent replacement was specified (the sample awaiting the reagent dispensing). Thus, the sample already dispensed when the reagent replacement was instructed is heated by the heater 110, and is measured within a set time after heating. Similarly, the sample being heated in the heater 110 when the reagent replacement was instructed is also measured within a set time after heating.

The second optical information obtainer 140 functions to obtain optical information from the measurement sample. The second optical information obtainer 140 is configured by a cuvette feeder 141, and sensor 142 disposed below the cuvette feeder 141, as shown in FIG. 5.

The sensor 142 of the second optical information obtainer 140 is capable of optically measuring (main measurement) of a measurement sample within a cuvette 200 under a plurality of conditions. The second optical information obtainer 140 is electrically connected to the controller 4a of the control unit 4, and transmits data (optical information) obtained by the second optical information obtainer 140 to the controller 4a of the control unit 4. Thus, the control unit 4 analyzes the data (optical information) received from the second optical information obtainer 140 based on the analysis result of the already obtained data (optical information) from the first optical information obtainer 90.

The 660 nm wavelength light emitted from the beam splitter optical fiber 102 is used as the main wavelength when measuring Fbg (fibrinogen content), PT (prothrombin time), and APTT (active partial thromboplastin time). The 800 nm wavelength light is a sub wavelength used when measuring Fbg, PT, and APTT. The 405 nm wavelength is used for measuring ATIII, which is a measurement item in the synthetic substrate method, and 800 nm wavelength light is used to measure D dimer and FDP, which are measurement items in the immunoturbidity method. The wavelength for measuring platelet coagulation is 575 nm.

The urgent sample section 150 is provided for the analysis and processing for samples requiring urgent attention, as shown in FIGS. 3 through 5. The urgent sample section 150 is configured so as to allow an urgent sample to interrupt an on-going sample analysis process of a sample supplied from the transporting unit 3. The fluid flow section 160 is provided to supply a fluid such as washing fluid to nozzles provided in each dispensing arm (sample dispensing arm 800 and reagent dispensing arm 130) during the shutdown process of the sample analyzer 1.

The cuvette supplying device 170 is capable of sequentially supplying a plurality of cuvettes 200 directly loaded by the user to the cuvette transporting section 70. As shown in FIGS. 3 through 5, the cuvette supplying device 170 includes a first hopper 171a, second hopper 171b that is smaller than the first hopper 171a and supplied cuvettes 200 from the first hopper 171a, two guide plates 172 for supplying cuvettes 200 from the second hopper 171b, support table 173 disposed below the bottom end of the two guide plates 172, and catchers 174 provided at predetermined spacing from the support table 173. The cuvettes 200 within the first hopper 171a move through the second hopper 171b, which is smaller than the first hopper 171a, and fall from the top of the two guide plates 172 toward the support table 173. The support table 173 functions to rotate the cuvettes 200 that have smoothly dropped along the guide plates 172 to a position at which the cuvette 200 is able to be grabbed by the catcher 174. The catcher 174 is provided to supply to the cuvette transporting section 70 those cuvettes 200 which have been moved by the support table 173.

As shown in FIGS. 3 through 5, the measuring unit 2 is provided with a disposal hole 181 for disposing of the cuvettes 200 (refer to FIGS. 3 and 5), and a waste box 182 disposed below the disposal hole 181 at a predetermined distance from the previously mentioned catcher 174. The catcher 174 disposes of the cuvette 200 on the cuvette transporting table 71 of the cuvette transporting section 70 through the disposal hole 181 (refer to FIGS. 3 and 5) and into the waste box 182. That is, the catcher 174 both supplies and disposes of the cuvettes 200.

The analysis operation of the sample analyzer 1 is described below with reference to FIGS. 4 and 5. The operation of performing measurements using the coagulation time method is described below.

The sample analyzer 1 is initialized by switching ON the respective power sources of the measuring unit 2 and control unit 4 of the sample analyzer 1 shown in FIG. 4. Thus, an operation is performed to return the devices for moving the cuvettes 200 and each dispensing arm (sample dispensing arm 80 and reagent dispensing arm 130) to their initial positions, and the software stored in the controller 4a of the control unit 4 is initialized.

Then, the transporting unit 3 shown in FIG. 5 moves the rack 251 loaded with test tubes 250 containing samples. In this way the rack 251 at the rack placement region 3a is moved to a position corresponding to the aspirating position 2a of the measuring unit 2.

Next, a predetermined amount of the sample is aspirated from the test tube 250 by the sample dispensing arm 80. Then, the sample dispensing arm 80 is moved above the cuvette 200 held on the cuvette transporting table 71 of the cuvette transporting section 70. Thereafter, part of the sample is allocated into the cuvette 200 by discharging sample from the dispensing arm 80 into the cuvette 200 on the cuvette transporting table 71.

The cuvette transporting table 71 is then rotated, and the cuvette 200 to which the sample was dispensed is moved to a position at which measurements are able to be performed by the first optical information obtainer 90. In this way optical information is obtained from the sample when the first optical information obtainer 90 optically measures the sample. Specifically, data, which is composed of electrical signals derived from the five types of light (340 nm, 405 nm, 575 nm, 660 nm, 800 nm) transmitted through the sample within the cuvette 200 held by the cuvette holder 72 (refer to FIG. 5) of the cuvette transporting table 71, are transmitted to the controller 4a of the control unit 4. In this way optical information (first optical information) is obtained from the sample when the first optical information obtainer 90 optically measures the sample.

The controller 4a of the control unit 4 calculates the light absorption of the sample using the received data (first optical information), and calculates the presence and concentration of the interference substances (chyle, hemoglobin, bilirubin)

in the sample, using the received data (first optical information). Specifically, the controller 4a of the control unit 4 calculates the light absorption of the sample based on the optical information (first optical information) obtained using four types of light (405 nm, 575 nm, 660 nm, 800 nm) emitted from the lamp unit 100, and stores the light absorption in the RAM 401c.

Thereafter, a determination is made as to whether or not the light absorption at the main wavelength is below a threshold value among the light absorptions stored in the RAM 401c. Specifically, when the sample measurement item is an item using the coagulation time method such as PT, APTT, Fbg or the like, a determination is made as to whether or not the light absorbance calculated from the first optical information measured using light of the main 660 nm wavelength is less than a threshold value (for example, 2.0).

When the light absorption at the main wavelength calculated from the first optical information measured by the first optical information obtainer 90 is less than the threshold value, the cuvette 200 is moved from the cuvette transporting table 71 to the heater 110 by the cuvette transporting section 120. Then, the cuvette 200, which contains sample that has been heated to approximately 37 degrees Centigrade by the heater 110, is grabbed by the catcher 121 of the cuvette transporting section 120. While the cuvette 200 is held by the catcher 121, the reagent dispensing arm 130 is actuated and the reagent within the reagent container 300 placed on the reagent table (first reagent table 11 or second reagent table 12) is added to the cuvette 200. The sample and reagent within the cuvette 200 are then agitated by the oscillation function of the catcher 121. Thus, a measurement sample is prepared. The cuvette 200 containing the measurement sample is then directly moved to the cuvette feeder 141 of the second optical information obtainer 140.

The sensor 142 of the second optical information obtainer 140 obtains optical information (second optical information) from the measurement sample by optically measuring (main measurement) the measurement sample within a cuvette 200 under a plurality of conditions. Specifically, light is first emitted from the beam splitter optical fiber 102 of the lamp unit 100 toward the cuvette 200 of the cuvette feeder 141. Five different wavelength of light (340 nm, 405 nm, 575 nm, 660 nm, 800 nm) are emitted from the beam splitter optical fiber 132. Thus, data are obtained which are electrical signals corresponding to the light of each wavelength that was emitted from the beam splitter optical fiber 132 and passed through the cuvette 200 and the measurement sample within the cuvette sample.

The electrical signal data corresponding to the light of the five different wavelengths are sequentially transmitted to the controller 4a of the control unit 4. In this way optical information (second optical information) is obtained from the sample when the second optical information obtainer 140 optically measures the sample.

When the light absorption at the main wavelength calculated from the first optical information measured by the first optical information obtainer 90 is greater than the threshold value, a determination is made as to whether or not the light absorption at the sub wavelength calculated from the first optical information measured by the first optical information obtainer 90 is less than the threshold value. Specifically, when the sample measurement item is an item using the coagulation time method such as PT, APTT, Fbg or the like, a determination is made as to whether or not the light absorbance calculated from the first optical information measured using light of the main 800 nm wavelength is less than a threshold value (for example, 2.0).

When the light absorption at the sub wavelength calculated from the first optical information measured by the first optical information obtainer 90 is less than the threshold value, optical information (second optical information) is obtained from the measurement sample by the second optical information obtainer 140.

However, when the light absorption at the sub wavelength calculated from the first optical information measured by the first optical information obtainer 90 is greater than the threshold value, it is determined that analysis with high reliability is difficult due to the excessive influence of interference substances (bilirubin, hemoglobin, and chyle) in the sample, and therefore the main measurement is terminated. Thus, wasteful use of reagent is prevented since a measurement specimen is not prepared by adding reagent to a sample that is not able to be analyzed due to the excessive influence of interference substances. The determination that highly reliable measurement is difficult (the cause of main measurement termination) occurs, for example, when light is blocked from passing through the sample due to the presence of large quantities of interference substances in the sample detected by the first optical information obtainer 90, such that the transmittance light passing through the sample is essentially undetectable.

After the second optical information has been obtained (main measurement) by the second optical information obtainer 140, the second optical information of the measurement sample measured at the main wavelength is transmitted to the controller 4a of the control unit 4 from among the plurality of the second optical information measured by the second optical information obtainer 140 and analyzed by an application program 404a installed on the hard disk 401d of the controller 4a. For example, when the sample measurement item is PT, the second optical information measured using the light of the main wavelength 660 nm is transmitted to the controller 4a of the control unit 4. Thereafter, the controller 4a, which has received the second optical information acquired at the main wavelength, outputs the analysis result based on this second optical information.

Similarly, after the second optical information has been obtained (main measurement) by the second optical information obtainer 140, the second optical information of the measurement sample measured at the sub wavelength is transmitted to the controller 4a of the control unit 4 from among the plurality of the second optical information measured by the second optical information obtainer 140 and analyzed by an application program 404a installed on the hard disk 401d of the controller 4a. Specifically, when the sample measurement item is PT, the second optical information measured using the light of the main wavelength 800 nm is transmitted to the controller 4a of the control unit 4. Thereafter, the controller 4a, which has received the second optical information acquired at the sub wavelength, outputs the analysis result based on this second optical information.

After the analysis is completed by the controller 4a of the control unit 4, the obtained analysis result is displayed on the display 4b of the control unit 4. This completes the analysis of a sample by the sample analyzer 1.

Figure 21:
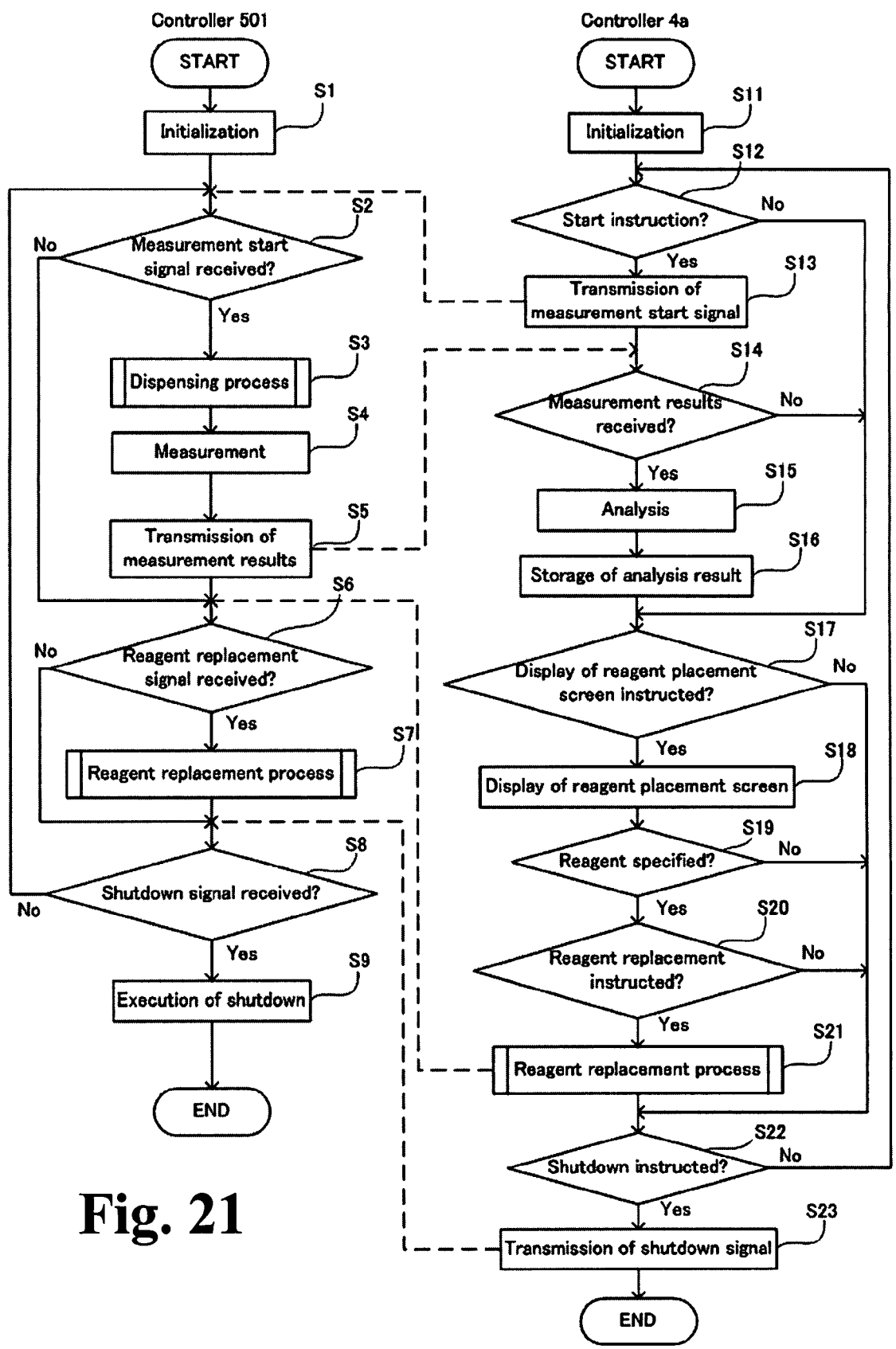
FIG. 21 is a flow chart illustrating the measuring process performed by the controller of the measuring unit and the controller of the control unit of the embodiment of the sample analyzer of the present invention.

FIG. 21 is a flow chart illustrating the flow of the measuring process of the controller 501 of the measuring unit 2 and the controller 4a of the control unit 4 in the sample analyzer 1. The flow of the measuring process of the controller 501 and controller 4a of the sample analyzer 1 of the present embodiment is described below with reference to FIGS. 1, 3, 7, and 21.

When the power source (not shown in the drawing) of the measuring unit 2 is turned ON, the controller 501 is initialized (program initialization) and an operation check is performed of each part of the measuring unit 2 in step S1. When the power source (not shown in the drawing) of the control unit 4 is turned ON, the controller 4a is initialized (program initialization) in step S11. When the initialization of the controller 501 is completed, the controller 501 requests an initialization completed signal indicating the initialization has been completed from the controller 4a; when this initialization completed signal is received, the barcode reader 350 is controlled so as to read the barcodes of all reagents and reagent racks placed in the reagent storing part 6. The read barcode information is transmitted from the controller 501 to the controller 4a, and stored on the hard disk 401d of the controller 4a.

In step S12, the menu screen (not shown in the drawing) is displayed on the display 4b, the user presses the start button displayed on the menu screen, and a measurement start signal is transmitted from the controller 4a to the controller 501 in step S13. When the start button is not pressed in step S12, the process continues to step S17.

In step S2, a determination is made by controller 501 as to whether or not a measurement start signal has been received; the process continues to step S3 when it is determined that a measurement start signal has been received, and the process continues to step S6 when it is determined that a measurement start signal has not been received.

In step S3, a process is performed to dispense reagent to the sample in the cuvette 200. In step S4, the sample to which the reagent was dispensed is measured by the first optical information obtainer 90 and the second optical information obtainer 140, then, the measurement results are transmitted from the controller 501 to the controller 4a in step S5.

In step S14, a determination is made by the controller 4a as to whether or not the measurement results have been received; the process continues to step S15 when the measurement results have been received, and the process moves to step S17 when the measurement results have not been received. In step S15, the measurement results are analyzed by the controller 4a, and these analysis results are stored on the hard disk 401d in step S16.

In step S17, the controller 4a determines whether or not there is a display command to display the reagent placement screen 410 (whether or not the reagent button (not shown in the drawing) has been pressed on the main menu to display the reagent placement screen); the process advances to step S18 when there is a display command to display the reagent placement screen 410, and the process advances to step S22 when there is not a display command to display the reagent placement screen 410. In step S18, the controller 4a displays the reagent placement screen 410. When the reagent placement screen 410 is displayed, the controller 4a displays the necessary information in the first reagent display region 421, second reagent display region 422, and reagent information display region 430 in the reagent placement screen 410 based on the barcode information read in step S1. (refer to FIG. 7).

In step S19, the controller 4a determines whether or not a replacement reagent has been specified on the reagent placement screen 410 shown in the display 4b which has a touch panel function. The reagent specification is described in detail below. That is, the user first confirms the placement of the reagent by referencing the reagent placement display region 420 of the reagent placement screen 410 shown in FIG. 7. The user selects an optional reagent with a finger by directly touching the first reagent display region 421 or second reagent display region 422 that displays the reagent among a plurality of first reagent display regions 421 and second reagent display regions 422. After the user has determined the reagent to be replaced, the user selects either the first reagent display region 421 or second reagent display region 422 that displays the selected reagent to be replaced. The process advances to step S20 when the controller 4a has determined there is a reagent specification in step S19, and the process advances to step S22 when the controller 4a determines that no reagent has been specified. In FIG. 7, the reagent [PT-TPC+] at reagent position [A15-6] is specified, and the attribute information of reagent [PT-TPC+] is displayed in the reagent information display region 430.

When it is determined in step S20 that reagent replacement has been instructed, the controller 4a performs the reagent replacement process and a reagent replacement signal is transmitted from the controller 4a to the controller 501 in step S21. When it is determined in step S20 that reagent replacement has not been instructed, the process continues to step S22.

In step S22, the controller 4a determines whether or not shutdown has been instructed (whether or not the shutdown button (not shown in the drawing) on the menu screen has been pressed); the process continues to step S23 when shutdown has been instructed, and the process returns to step S12 when shutdown has not been instructed. In step S23, a shutdown signal is transmitted from the controller 4a to the controller 501, the control unit 4 shuts down and the process ends.

In step S6, the controller 501 determines whether or not a reagent replacement signal has been received; the process continues to step S7 when it is determined that a reagent replacement signal has been received, and the process continues to step S8 when it is determined that a reagent replacement signal has not been received. In step S7, the controller 501 performs the reagent replacement process.

In step S8 a determination is made as to whether or not a shutdown signal has been received; the process advances to step S9 when a shutdown signal has been received, and the process returns to step S2 when a shutdown signal has not been received. In step S9, the measuring unit 2 shuts down and the process ends.

In the flow of the measuring process performed by the controller 501, steps S3, S4, and S7 are parallel processes and are performed in parallel. In the flow of the measuring process performed by the controller 4a, steps S15, S18, and S21 are parallel processes and are performed in parallel.

FIG. 22 is a flow chart illustrating the details of the reagent replacement process of the controller 4a executed in step S21 of the flow chart shown in FIG. 21. FIG. 23 is a flow chart illustrating the details of the reagent replacement process of the controller 501 executed in step S7 of the flow chart shown in FIG. 21. The flows of the reagent replacement processes performed by the controller 4a and controller 501 of the sample analyzer 1 of the present embodiment are described below referring to FIGS. 3, 7, 22, and 23.

In step S41 of FIG. 23, the controller 501 determines whether or not there is a sample awaiting reagent dispensing which uses the reagent on the reagent table that includes racks holding specified reagent (hereinafter referred to as "replacement reagent table"); if there is a sample awaiting reagent dispensing which uses the reagent on the reagent replacement table when the reagent replacement signal has been received, the reagent is dispensed to the sample in step S42. Reagent is dispensed from the reagent replacement table to all samples awaiting reagent dispensing which use reagent on the reagent replacement table by repeating steps S41 and S42. Thus, if there are samples awaiting reagent dispensing which use reagent from the reagent replacement table when reagent replacement has been instructed, reagent is dispensed to the samples prior to executing reagent replacement. Reagent must be dispensed after a predetermined time has elapsed once a sample has been dispensed to the cuvette 200 and measurement has been started, and if that sequence does not happen properly, the sample is not able to be used for measurement and must be scrapped. Accordingly, samples for which measurement has started (samples awaiting reagent dispensing) must be subjected to predetermined processing and measurements must be completed without interruption. The controller 501 executes the steps subsequent to step S43 to perform the reagent replacement operation when there are no samples which use reagent from the reagent replacement table among the samples awaiting reagent dispensing when reagent replacement has been instructed. That is, when there are no samples awaiting reagent dispensing, or all samples use reagent from the reagent that is not the reagent replacement table, the reagent replacement operation is able to be performed since there is no need to access the reagent replacement table. Therefore, whether or not there is a sample which uses reagent from the reagent replacement table among the samples awaiting reagent dispensing when reagent replacement has been instructed, no samples are wasted and reagent replacement is performed promptly since the samples awaiting reagent dispensing are not invalidated.

When it has been determined in step S41 that none of the samples awaiting reagent dispensing will use reagent from the reagent replacement table, then in step S43 the controller 501 rotates the reagent replacement table and move the first reagent container rack 310 or second reagent container rack 320 holding the specified reagent to the pick up position (below the first cover 30 or second cover 40) by controlling the first drive part 502 and second drive part 503. In this process, the controller 501 issues a movement command to the drive circuit of the reagent replacement table. When this command is received by the drive circuit, the drive circuit sets a reagent replacement flag in an internal status register. That is, the reagent replacement status is set ON for the reagent replacement table that includes the reagent specified by the user for replacement. Either the reagent replacement status for the first reagent table 11 or the reagent replacement status for the second reagent replacement table 12 is set ON. When the reagent container rack holding the specified reagent is moved to the pick up position, the controller 501 transmits a movement completion signal to the controller 4*a* that indicates the reagent container rack holding the specified reagent has moved to the pick up position in step S44. The controller 501 determines the amount of rotational movement of each reagent table 11 and 12 from the origin position of the first reagent table 11 and second reagent table 12 by counting the number of pulses of the pulse drive signals supplied to the first drive part 502 and second drive part 503. Therefore, the controller 501 recognizes that the first reagent table 11 and second reagent table 12 have moved to the pick up position by the amount of movement from the origin position, and generates a movement completion signal based on this recognition.

When the movement completion signal is transmitted from the controller 501 to the controller 4*a*, the controller 4*a* determines whether or not the movement completion signal has been received in step S31 of FIG. 22. When it is determined in step S33 that the movement completion signal has been received, the user is indicated that the reagent container rack holding the specified reagent has been moved to the pick up position in step S32. Specifically, when the reagent container rack holding the specified reagent has been moved to the pick up position, the LED indicator 61 or LED indicator 62 in the reagent replacing part 7, which has been emitting red light while the reagent container rack is moving, now emits blue light. Thus, the user is indicated that the reagent container rack that holds the specified reagent has been moved to the pick up position.

The user releases the locking device for the cover of the reagent replacement table to perform the reagent replacement operation. A lock release signal is transmitted from the lock sensor of the cover to the controller 501, and in step S45 the controller 501 determines whether or not the cover lock has been released. In the case of the first cover 30, the cover lock release operation entails the user rotating the handle 32 of the first cover 30 in the opposite direction to the arrow A direction (refer to FIG. 13) to unlock the first cover 30. To unlock the second cover 40, the user rotates the handle 42 of the second cover 40 in the opposite direction to the arrow C direction (refer to FIG. 13). The determination that the lock has been released is performed as follows. When the first cover 30 or second cover 40 has been unlocked by rotating the handle 32 or handle 42 from the locked state in the opposite direction to the arrow A direction or the opposite direction to the arrow C direction, there is a release of the pressing force of the pressing piece 35*b* or 45*b* that pushes the microswitch 51*a* of the first sensor 51 or the microswitch 52*a* of the second sensor 52. Therefore, the microswitch 51*a* of the first sensor 51 or the microswitch 52*a* of the second sensor 52 detects the release of the cover lock, and either the first sensor 51 or second sensor 52 transmits a detection signal to the controller 501.

The reagent replacement operation performed by the user entails the user removing either the unlocked first cover 30 or unlocked second cover 40, and thereafter grasping and removing the handle 313 or 327) of the reagent container rack at the pick up position (below the first cover 30 or second cover 40). Then, the user replaces the reagent container 300 containing the specified reagent with a new reagent container 300 containing fresh reagent. Subsequently, the reagent container rack holding the replaced reagent is returned to the pick up position, and the user attaches and locks the first cover 30 or second cover 40. In the case of the first cover 30, the cover locking operation entails the user rotating the handle 32 of the first cover 30 in the arrow A direction (refer to FIG. 13) to lock the first cover 30. To lock the second cover 40, the user rotates the handle 42 of the second cover 40 in the arrow C direction (refer to FIG. 13).

A lock signal is transmitted from the lock sensor of the cover to the controller 501, and in step S46 the controller 501 determines whether or not the cover is locked. The determination of whether or not the cover is locked in step S46 is performed as follows. When the first cover 30 or second cover 40 has been locked by rotating the handle 32 or handle 42 from the unlocked state in the arrow A direction or the arrow C direction, the microswitch 51*a* of the first sensor 51 or the microswitch 52*a* of the second sensor 52 is pressed, and the first sensor 51 or second sensor 52 transmits a detection signal to the controller 501. Thus, it is determined that the cover is locked.

When the controller 501 has determined in step S46 that the first cover 30 or second cover 40 is locked, a barcode reading operation is performed in step S47. In the barcode reading operation, the controller 501 controls the first reagent container table 11 or second reagent container table 12, and the barcode reader 350 so as to have the barcode reader 350 read the barcodes of the first reagent container rack 310 or second reagent container rack 320 holding the replaced reagent. Specifically, when reading the second reagent container rack 320 and barcodes 300*a*, and 321*b* through 326*b* or 321*c* through 326*c* of the reagent containers 300 held in the second reagent container rack 320, the barcode 321*b* identifying the position information is initially read while the second reagent table 12 is rotated in the arrow G direction (counterclockwise direction). Thereafter, the barcode 300*a* identifying the reagent information or barcode 321*c* identifying absent container information is read, and subsequently the barcode 322*b* identifying position information is read. In this way the position information (barcodes 321*b* through 326*b*), and reagent information corresponding to the position information (barcode 300*a*) or absent container information (barcodes 321*c* through 326*c*) are alternately read.

When reading the barcodes 300*a*, and 311*b* through 312*b* or 311*c* through 312*c* of the first reagent container rack 310 and reagent containers 300 held in the first reagent rack 310, the second reagent table 12 is first rotated to have the gap 12*a* of the second reagent table 12 reach the position opposite the barcode reader 350. Thereafter, the barcode reader 350 alternately reads the position information (barcodes 311*b* through 312*b*), reagent information corresponding to the position information (barcode 300*a*), and absent container information (barcodes 311*c* through 312*c*) while the first reagent table 11 is rotating in the arrow G direction (counterclockwise direction) through the gap 12*a* (refer to FIG. 5) similar to when reading the second reagent container racks 320 and barcodes holding the second reagent container rack 320. The read position information, and reagent information corresponding to the position information or absent container information are transmitted to the controller 501 and stored in RAM 501*c*.

In step S48, the controller 501 transmits the barcode reading information stored in the RAM 501*c* to the controller 4*a*.

When the barcode reading information is transmitted from the controller 501 to the controller 4*a*, the controller 4*a* determines in step S33 whether or not the barcode reading information has been received. When the controller 4*a* determines that the barcode reading information has been received in step S33, the barcode reading information is stored on the hard disk 401*d* in step S34. In step S35, the controller 4*a* refers to the reagent master table, reagent lot master table, and container master table to obtain detailed information such as reagent name, type of container, lot number, and valid period and the like for all reagents in the reagent racks holding replaced reagent based on the barcode reading information (read position information, reagent information corresponding to the position information or absent container information) stored on the hard disk 401*d*. In step S36, the controller 4*a* displays the detailed information including position information, obtained reagent name, container type, lot number, and valid period in the first reagent display region 421 or second reagent display region 422 and reagent display region 430 of the reagent placement screen 410.

FIG. 24 is a flow chart illustrating the details of the dispensing process of the controller 501 executed in step S3 of the flow chart shown in FIG. 21. The flow of the dispensing process performed by the controller 501 of the sample analyzer 1 of the present embodiment is described below referencing FIGS. 3, 5, and 21.

First, in step S51, the controller 501 controls the sample barcode reader 3*c* to read the barcode adhered to the test tube 250 containing the sample transported by the transporting unit 3. In step S52, the controller 501 obtains an order based on the read barcode information, and the process continues to step S53. In step S53, the controller 501 determines whether or not the reagent replacement status has been turned ON for the first reagent table 11 or second reagent table 12. This process is performed by confirming the internal status registers of the drive circuit of the replacement reagent table by controller 501. In step S53 a determination is made that the reagent replacement status is turned ON for either the first reagent table 11 or the second reagent table 12, the process continues to step S54. When it has been determined in step S53 that neither reagent replacement status has been turned ON, the process continues to step S56. The order is described below. The order is information including the analysis items associated with the information specifying the sample. The order may be recorded on the host computer (not shown in the drawing) connected to the control unit 4, and is able to be stored manually by the user in the control unit 4. After the sample barcode has been read, the control unit 4 searches the orders stored in the control unit 4 and obtains a matching order using the sample ID as a key search term to the host computer. The order obtained by the control unit 4 is transmitted from the controller 4*a* of the control unit 4 to the controller 501 of the measuring unit 2, and the controller 501 obtains the order.

In step S56, the controller 501 controls the sample dispensing drive part 80*a* in accordance with the order, the sample contained in the test tube 250 transported by the transporting part 3 is aspirated by the sample dispensing arm 80, and the aspirated sample is dispensed into a cuvette 200 held by the cuvette holder 72 of the cuvette transporting table 71. In step S57, the controller 501 controls the reagent dispensing drive part 130*a*, and the reagent is aspirated through the holes 22*a*, 22*b*, or 22*c* of the outer wall 20 of the reagent storing part 6 by the reagent dispensing arm 130, and the aspirated reagent is dispensed into a cuvette 200 that has been heated.

When the controller 501 has determined that the reagent replacement status has been turned ON for either the first reagent table 11 or second reagent table 12 in step S53, a determination is made in step S54 as to whether or not the reagent analysis items specified in the order use a reagent held on the reagent replacement table. When it has been determined in step S54 that the reagent analysis items specified in the order do not use a reagent from the reagent replacement table, the process continues to steps S56 and S57, and the previously described processing is performed. When it has been determined in step S54 that the reagent analysis items specified in the order do use a reagent from the reagent replacement table, the obtained order is deferred in step S55. The processes of steps 51 through 55 are repeated until it has been determined that the analysis items specified in the order do not use a reagent from the reagent replacement table. The processes of steps S56 and S57A are sequentially executes for deferred order when it has been determined that the analysis items specified in an obtained order do not use a reagent from the reagent replacement table.

Thus, in the present embodiment, when reagent replacement is instructed, dispensing is suspended from the reagent table that includes the reagent specified for replacement, and dispensing is executed from the reagent table that does not include reagent specified for replacement.

Reagent replacement is performed in the above manner in the present embodiment.

In the present embodiment, as described above, when a reagent replacement is instructed, the reagent container 300 that contains the reagent the user wants to replace is moved to the pick up position by controlling the reagent table (first reagent table 11 or second reagent table 12) so as to move the reagent container 300 containing the specified reagent to the position at which it is able to be picked up.

In the present embodiment, a user confirms the placement of the reagent containers 300 arranged on the reagent tables and specified the reagents to be replaced by displaying the placement of the reagent containers 300 disposed on the first reagent table 11 or second reagent table 12 on the reagent placement screen 410 of the display 4*b*.

In the present embodiment, a user is able to easily specify at least one single reagent from the first reagent display region 421 or second reagent display region 422 of the reagent placement screen 410 via a configuration that allows at least one reagent to be specified on the reagent placement screen 410 as described above.

In the present embodiment, a user is able to confirm the attribute information of a specified reagent by displaying the attribute information of a specified reagent in the reagent placement display region 420 in the reagent information display region 430 of the reagent placement screen 410 as described above.

In the present embodiment, a user is able to easily manage reagents when a reagent has been replaced by obtaining reagent information from the barcode 300*a* of the reagent container 300 containing the replaced reagent using the barcode reader 350 after the reagent has been replaced.

In the present embodiment, the reagent information of a replaced reagent is able to be obtained even when the reagent that was replaced is different from the specified reagent placed in the same reagent container rack as the specified reagent by obtaining reagent information from the barcodes 300*a* of the all the reagent containers 300 held in the reagent container rack (first reagent container rack 310 or second reagent container rack 320) that holds the reagent container 300 containing the replaced reagent after the reagent has been replaced.

In the present embodiment, a reagent container rack that has been moved to the pick up position is able to be easily removed and a new reagent container 300 is able to be placed therein by opening the first cover 30 or second cover 40 since the first cover 30 and second cover 40 are configured so as to be openable at the pick up position of the reagent container rack that holds the reagent container containing a specified reagent.

Reagent information is able to be obtained automatically via the locks of the first cover 30 or second cover 40 without performing a special operation to obtain reagent information since reagent information of a replaced reagent is able to be automatically obtained by the barcode reader 350 when the lock status has been detected by the first sensor 51 or second sensor 52.

In the present embodiment, reagent placed in one of the first reagent table 11 and the second reagent table 12 is able to be replaced when a measurement sample is to be analyzed using reagent placed in the other table among the first reagent table 11 or second reagent table 12 by providing a first reagent table that is rotatable and places a plurality of reagent containers 300 in a circle, and a second reagent table that is disposed concentrically to the first reagent table and is also rotatable and places reagent containers 300 in a circle.

In the present embodiment, a user is able to easily confirm that a reagent has been moved to the pick up position since the user is indicated of the arrival of the specified reagent at the pick up positioned by the LED indicators 61 or 62.

The embodiments described here are to be considered as examples in all aspects and in no way limiting. The scope of the present invention is defined by the scope of the claims and not be the description of the embodiment, and includes all modifications within the scope of the claims and the meanings and equivalences therein.

For example, although the present embodiment is described by an example in which the reagent placement screen 410 is displayed on the display 4*a* of the control unit 4, the present invention is not limited to this configuration inasmuch as a display may also be provided for the measuring unit so that the reagent placement screen is able to be displayed on the display unit of the measuring unit.

Although a user manually unlocks and removes a cover (first cover 30 or second cover 40) in the example of the present embodiment, the present invention is not limited to this configuration inasmuch as the cover (first cover 30 or second cover 40) may be automatically unlocked when the reagent container rack (first reagent container rack 310 or second reagent container rack 320) holding the replacement reagent has been moved to the pick up position. In this case, the user is able to be indicated of the unlocked condition via the LED indicators 61 and 62, or on the display 4*b* of the control unit 4.

Although a user is indicated that the reagent container rack (first reagent container rack 310 or second reagent container rack 320) holding the replacement reagent has been moved to the pick up position by the LED indicator 61 or 62 in the present embodiment, the present invention is not limited to this configuration inasmuch as the user may also be indicated by the display 4*b* of the control unit 4.

Although reagent is specified for replacement or addition by a user pressing a reagent replacement-addition button 440*a* after selecting the first reagent display region 421 or second reagent display region 422 of the reagent placement screen 410 by hand in the example of the present embodiment, the present invention is not limited to this example. For example, reagent may also be specified for replacement or addition by a user pressing a reagent replacement-addition button 440*a* after selecting a reagent rack region on the reagent placement screen 410 corresponding to the first reagent container rack 310 or second reagent container rack 320 by hand.

Although the process of moving the reagent table is performed by the controller 501 in the example of the present embodiment, the process of moving the reagent table may be performed by the controller 4*a*.

What is claimed is:

1. A sample analyzer for analyzing a sample, comprising:
a holding section comprising a plurality of holding regions for holding reagent containers, each of the reagent containers containing a reagent, and being capable of moving the holding regions, wherein only a portion of the holding regions are populated with reagent containers;
an analyzing unit for analyzing a measurement sample prepared by mixing a sample and the reagent contained in the reagent container held by the holding section;
a reader for reading identification information attached to a reagent container held by the holding section;
an input device;
a display;
a controller configured to perform operations comprising:
controlling the display so as to display a screen showing a plurality of display areas corresponding to the plurality of holding regions respectively, the display areas being selectable,
obtaining reagent name information which represents the name of a reagent contained in a first reagent container, based on the identification information of the first container read by the reader;
selectively displaying the obtained reagent name information on a first display area corresponding to a first holding region which holds the first reagent container, wherein the display includes a second display area corresponding to an unpopulated holding region and wherein reagent name information is not displayed in the second display area;

receiving, through the input device, a selection of the second display area from the plurality of display areas; and controlling the holding section so as to move the second holding region to a container-addition position at which the a second reagent container is added to the holding section.

2. The sample analyzer of claim 1, wherein the screen includes an attribute information display area which is arranged separately from the plurality of display areas; and the controller is further configured to perform operations comprising:

obtaining, based on the identification information of the first reagent container, attribute information of the reagent in the first reagent container including the reagent name information, when the first display area has been selected, and displaying the obtained attribute information in the attribute information display area.

3. The sample analyzer of claim 1, wherein the controller is configured to control the holding section and the reader so as to read identification reagent information of the second reagent container after the second reagent container has been added to the holding section.

4. The sample analyzer of claim 3, wherein the holding section is configured to hold a plurality of reagent racks for holding the reagent containers, and wherein the controller is configured to control the holding section and the reader so as to read identification information attached to a reagent container held in a reagent rack which holds the a second reagent container.

5. The sample analyzer of claim 1, further comprising a cover for covering the holding section, wherein the cover is configured to be openable and closable at the container addition position.

6. The sample analyzer of claim 5, further comprising:

a locking part for locking the cover; and a locking state detector for detecting a locking state of the cover by the locking part, wherein the controller is configured to control the holding section and the reader so as to read identification information of the added second reagent container, when the locking state detector has detected the locking state after the second reagent container has been added to the holding section.

7. The sample analyzer of claim 5, further comprising a locking part for locking the cover, wherein the controller is configured to control the locking part so as to release the lock of the cover when the second holding region has arrived at the container addition position.

8. The sample analyzer of claim 1, wherein the holding section comprises: a rotatable first holding part for holding reagent containers circularly; and a rotatable second holding part for holding reagent containers circularly, and wherein the second holding part is arranged concentrically relative to the first holding part.

9. The sample analyzer of claim 1, further comprising an indicator for indicating that the second holding region has arrived at the container addition position.

10. The sample analyzer of claim 7, further comprising an indicator for indicating that the lock of the cover by the locking part has been released by the controller.

11. The sample analyzer of claim 1, wherein the controller is configured to perform operations comprising:

receiving, through the input device, a selection of the first display area from the plurality of display areas shown on the screen; and controlling the holding section so as to move the first holding region to the container addition position in order to replace the first reagent container on the first holding region.

* * * * *